United States Patent [19]
Dunahay et al.

[11] Patent Number: 5,661,017
[45] Date of Patent: *Aug. 26, 1997

[54] METHOD TO TRANSFORM ALGAE, MATERIALS THEREFOR, AND PRODUCTS PRODUCED THEREBY

[76] Inventors: Terri Goodman Dunahay, 2710 Arbor Glen Pl., Boulder, Colo. 80304; Paul G. Roessler, 15905 Ellsworth Pl., Golden, Colo. 80401; Eric E. Jarvis, 3720 Smuggler Pl., Boulder, Colo. 80303

[*] Notice: The term of this patent shall not extend beyond the expiration date of Pat. No. 5,559,220.

[21] Appl. No.: 404,732

[22] Filed: Mar. 15, 1995

Related U.S. Application Data

[63] Continuation-in-part of Ser. No. 120,938, Sep. 14, 1993, abandoned.

[51] Int. Cl.$^6$ .......................... A01H 13/00; C12N 1/13; C12N 15/29; C12N 15/31; C12N 15/79
[52] U.S. Cl. .................. 435/172.3; 435/69.1; 435/70.1; 435/71.1; 435/257.2; 435/320.1; 435/6; 435/420; 536/23.6; 536/23.7; 536/24.1; 800/205
[58] Field of Search .................. 435/69.1, 70.1, 435/71.1, 172.3, 240.4, 320.1, 257.2; 536/24.1, 23.6, 23.7; 800/205

[56] References Cited

U.S. PATENT DOCUMENTS

| | | | |
|---|---|---|---|
| 4,710,464 | 12/1987 | Belagaje et al. | 435/91 |
| 5,034,322 | 7/1991 | Rogers et al. | 435/172.3 |
| 5,100,792 | 3/1992 | Sanford et al. | 435/172.1 |
| 5,270,175 | 12/1993 | Moll | 435/41 |
| 5,316,931 | 5/1994 | Donson et al. | 435/172.3 |
| 5,559,220 | 9/1996 | Ohlrogge et al. | 536/23.6 |

FOREIGN PATENT DOCUMENTS

| | | |
|---|---|---|
| 0 108 580 A1 | 5/1984 | European Pat. Off. . |
| 0469810 | 2/1992 | European Pat. Off. . |

OTHER PUBLICATIONS

Barclay et al., 1986, Microalgae Culture Collection 1986–1987, Solder Energy Research Institute, Golden, CO. SERI/SP–232/3079.

Bingham et al., 1989, FEMS Microbiol. Lett., 65:77–82.

Brown et al., in *Biodiesel from Aquatic Species –Project Report: FY 1993*; NREL/TP–422–5726, UC Category:244, DE94000275, 1994, pp. 15–28.

Cheney, in *Economically Important Marine Plants of the Atlantic: Their Ecology and Cultivation*, (C. Yarish et al., eds.), Conn. Sea Grant College Program, 1990, pp. 15–24.

Day et al., 1990, Physiol. Plant., 78:254–260.

Dunahay et al., 1992, App. Biochem. Biotechnol., 34/35:331–339.

Goldschmidt–Clermont, 1991, Nucleic Acids Res., 19:4083–4089.

Hall et al., 1993, Gene, 24:75–81.

Hasnain et al., 1985, Mol. Cell. Biol., 5:3647–3650.

Jarvis et al., 1992, J. Phycol., 28:356–362.

Jarvis et al., 1991, Curr. Genet., 19:317–321.

Kindle et al, 1989, J. Cell Biol., 109:2589–2601.

Kurtzmann et al., 1991, J. Phycol., 27 Supp.:(Abstract No. 232), p. 42.

Mayfield, in *Transgenic Plants –Fundamentals and Applications* (A. Hiatt, ed.), Marcel Dekker, Inc., New York, N.Y., 1993, pp. 115–131.

Reimann et al., 1963, Phycologia, 3:75–84.

Roessler et al., in *Enzymatic Conversion of Biomass for Fuels Production*, (M. Himmel et al., eds.); ACS Symposium Series 566, American Chemical Society, Washington, D.C., 1994, pp. 256–270.

Roessler et al., 1993, J. Biol. Chem., 268:19254–19259.

Livne et al. 1990, Plant Cell Physiol. 31(6):851–858.

Roessler et al. 1992, Plant Physiol. 99 (Suppl. 1):19.

Roessler, P. 1990, Plant Physiol. 92:73–78.

Blowers et al. 1990, Plant Cell 2:1059–1070.

Blowers et al. 1989. Plant Cell 1:123–132.

Jarvis et al. 1991. J. Phycol. 27 (Suppl. 3): 34.

Douglas et al. 1994, J. Phycol. 30(2):329–340.

Douglas et al. 1991, J. Mol. Evol. 33(3):267–273.

Primary Examiner—David T. Fox
Attorney, Agent, or Firm—Edna M. O'Connor; Ruth Eure

[57] ABSTRACT

Disclosed is a method to transform chlorophyll C-containing algae which includes introducing a recombinant molecule comprising a nucleic acid molecule encoding a dominant selectable marker operatively linked to an algal regulatory control sequence into a chlorophyll C-containing alga in such a manner that the marker is produced by the alga. In a preferred embodiment the algal regulatory control sequence is derived from a diatom and preferably *Cyclotella cryptica*. Also disclosed is a chimeric molecule having one or more regulatory control sequences derived from one or more chlorophyll C-containing algae operatively linked to a nucleic acid molecule encoding a selectable marker, an RNA molecule and/or a protein, wherein the nucleic acid molecule does not normally occur with one or more of the regulatory control sequences. Further specifically disclosed are molecules pACCNPT10, pACCNPT4.8 and pACCNPT5.1. The methods and materials of the present invention provide the ability to accomplish stable genetic transformation of chlorophyll C-containing algae.

31 Claims, 2 Drawing Sheets

5,661,017

METHOD TO TRANSFORM ALGAE, MATERIALS THEREFOR, AND PRODUCTS PRODUCED THEREBY

CROSS REFERENCE TO RELATED APPLICATION

The present application is a continuation-in-part of U.S. patent application Ser. No. 08/120,938 entitled "Gene Encoding Acetyl-CoA Carboxylase from *Cyclotella cryptica*" filed Sep. 14, 1993, now abandoned, which is incorporated by reference herein in its entirety.

The United States Government has rights in this invention under contract No. DE-AC36-83CH10093 between the United States Department of Energy and the National Renewable Energy Laboratory, a division of the Midwest Research Institute.

FIELD OF THE INVENTION

The present invention relates to the field of genetic transformation of algae.

BACKGROUND OF THE INVENTION

The use of algae in a variety of industrial processes for commercially important products is known and/or has been suggested. For example, algae have been used to make pigmentation agents, such as carotenoids; nutritional supplements, such as omega-3 fatty acids; and pharmaceuticals. Use of algae in mariculture as a food source for fish and crustaceans is also well known. Algae have also been suggested for use in the production of starting materials for the production of a diesel fuel substitute. Further, algae have been suggested for use in pollution control, such as for the uptake of carbon dioxide and in bioremediation applications.

Some wild-type algae are suitable for use in these various applications. However, it is recognized that by modification of algae to improve particular characteristics useful for the above-referenced applications, the relevant processes are more likely to be commercially viable. To this end, algal strains have been developed which have improved characteristics over wild-type strains. Such developments have been made by traditional techniques of screening and mutation and selection. Further, recombinant techniques have been widely suggested for algae. However, for a variety of reasons, recombinant transformation techniques have not been successfully developed for wide scale development of algae.

Over the past decade, genetic transformation has become routine for many organisms, including bacteria, yeast, mammalian cells and some higher plants. However, there has been little success mn developing transformation systems for eucaryotic microalgae, due partly to the recalcitrance of commonly-used algal species to standard transformation techniques and genetic markers. This phenomenon is likely to be due to the difficulty of introducing foreign DNA into the algal cell through the cell wall and to poor expression of commonly used transformation markers, such as neomycin phosphotransferase or other antibiotic resistance genes, by the algae. To date, the only eucaryotic microalgae for which there are reproducible transformation systems are the single-celled green alga *Chlamydomonas reinhardtii* and a closely related colonial species *Volvox carterii*. However, successful transformation of these organisms to date has required the use of homologous genes as selectable transformation markers. These protocols often require the development of auxotrophic mutants which can be transformed with plasmids containing wild-type homologous genes, rendering the cells prototrophic.

In view of the above discussion, a need exists for a genetic transformation system which is widely useful in algae.

SUMMARY OF THE INVENTION

The present invention includes a method to transform chlorophyll C-containing algae which includes introducing a recombinant molecule comprising a nucleic acid molecule encoding a dominant selectable marker operatively linked to an algal regulatory DNA sequence into a chlorophyll C-containing alga in such a manner that the marker is produced by the alga. In a preferred embodiment the chlorophyll C-containing alga is a diatom and in more preferred embodiments is of a genus selected from the group consisting of Cyclotella and Navicula. In a further embodiment, the method can include introducing a recombinant molecule comprising a nucleic acid molecule encoding a product which is operatively linked to an algal regulatory control sequence into the alga such that the product is produced by the alga. In further preferred embodiments, the regulatory control sequences can include a *Cyclotella cryptica* acetyl-CoA carboxylase regulatory control sequence.

A further embodiment of the present invention includes a chimeric molecule which includes one or more regulatory control sequences derived from one or more chlorophyll C-containing algae operatively linked to a nucleic acid molecule encoding a selectable marker, an RNA molecule, or a protein, and wherein the nucleic acid molecule is not naturally associated with one or more of the regulatory control sequences. In a further preferred embodiment, the regulatory control sequences in the chimeric molecule are derived from a diatom, and preferably *Cyclotella cryptica*.

A further embodiment of the present invention includes a method to produce a recombinant chlorophyll C-containing algal strain which is transformed with a nucleic acid molecule encoding a dominant selectable marker in such a manner that the marker is produced by the strain. The method includes culturing the transformed strain in the presence of a compound that is toxic to algae not transformed by the marker nucleic acid molecule and to which the dominant selectable marker provides resistance, and subsequently isolating from the culture an algal strain that is capable of growing in the presence of the compound.

Further embodiments of the present invention include nucleic acid molecules which include nucleic acid sequences identified as SEQ ID NOS:1,2 or 3, or portions thereof having a regulatory function corresponding to the nucleic acid sequences of the SEQ ID NOS:1,2 or 3.

DETAILED DESCRIPTION OF THE INVENTION

Figure 1:
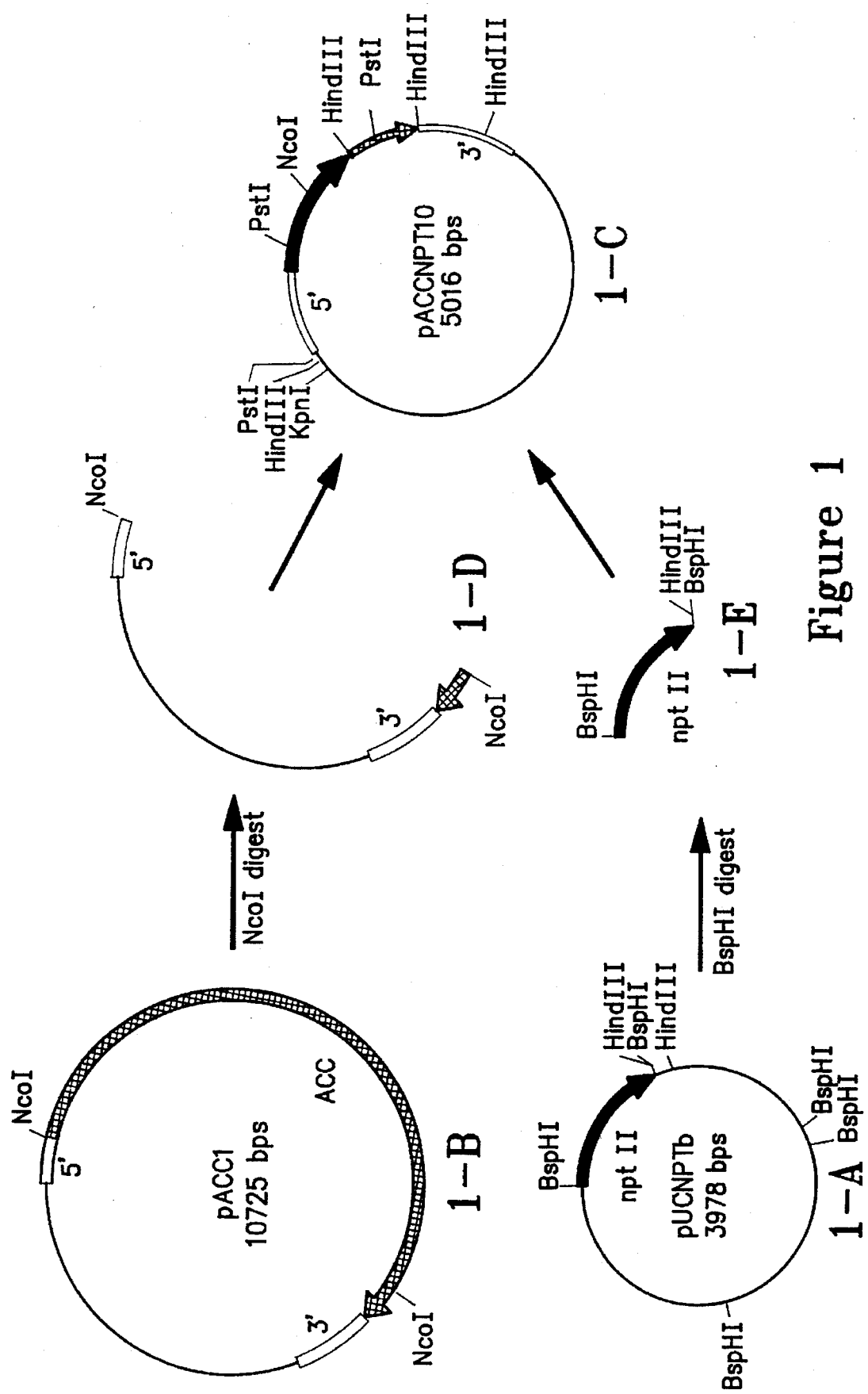
FIGS. 1A–1E illustrate the construction of recombinant molecule pACCNPT10.

The present invention includes a method to transform a chlorophyll C-containing alga by introducing a recombinant molecule into the chlorophyll C-containing alga. The recombinant molecule includes a nucleic acid molecule encoding a dominant selectable marker operatively linked to an algal regulatory control sequence such that, when introduced into a chlorophyll C-containing alga, the marker is produced by the alga. The present method has the significant advantage of providing a method for the transformation of algae without the need for auxotrophic strains. Further, the present method has been shown to produce stable transformants.

The term chlorophyll C-containing algae refers to the group of algal classes which contain the accessory photosynthetic pigments chlorophyll $C_1$ and/or chlorophyll $C_2$. As such, this term encompasses the classes Bacillariophyceae, Chrysophyceae, Phaeophyceae, Xanthophyceae, Raphidophyceae, Prymnesiophyceae and Cryptophyceae. In a preferred embodiment, the chlorophyll C-containing algae include the class Bacillariophyceae, or diatoms. In a further preferred embodiment, the chlorophyll C-containing algae include the genera Cyclotella, Navicula, Cylindrotheca, Phaeodactylum, Amphora, Chaetoceros, Nitzchia and Thalassiosira and more preferably the genera Cyclotella and Navicula. In a further preferred embodiment, the chlorophyll C-containing algae include the species *Cyclotella cryptica* and *Navicula saprophila.*

Without intending to be bound by theory, it is believed that the chlorophyll C-containing algae, including Cyclotella and Navicula, have characteristics that make them amenable to genetic transformation, particularly as compared to green algal strains such as Chlamydomonas. Attempts to transform Chlamydomonas with heterologous (i.e., bacterial or fungal) genes have met with little success. The *Chlamydomonas* genome is very GC-rich, which may be reflected in codon bias and poor expression of foreign genes. Diatoms exhibit GC contents more similar to that of many bacteria, indicating that these strains may be more capable of efficiently expressing bacterial marker genes.

As noted above, a recombinant molecule of the present invention includes a nucleic acid sequence encoding a dominant selectable marker. (It is to be noted that the term "a" or "an" entity refers to one or more of that entity; as such, the terms "a" (or "an"), "one or more" and "at least one" can be used interchangeably herein.) As used herein, the term "dominant selectable marker" refers to a protein or nucleic acid which confers upon an alga resistance to a compound to which the alga would otherwise be sensitive. In one embodiment, the dominant selectable marker can be a marker that is heterologous to the alga being transformed (i.e., a protein or nucleic acid derived from a species different from the alga being transformed that confers resistance to the compound being used to identify transformed algae). In another embodiment, a dominant selectable marker can be a homologous mutant marker (i.e., a protein or nucleic acid that is derived from the same species as the alga being transformed but which is modified so as to confer resistance to the compound to be used in selection of transformed algae). Thus, a dominant selectable marker is useful in identifying when algal strains have been successfully transformed because strains subjected to transformation techniques can be cultured in the presence of the compound to which the dominant selectable marker confers resistance. If a strain is able to grow in the presence of the compound, then successful transformation has occurred.

In accordance with the present invention, strains which have been subjected to transformation techniques can be cultured in the presence of the compound to which a dominant selectable marker confers resistance or as noted below, can be cultured to produce a product, under conditions effective to identify resistance or produce a product. Effective conditions include, but are not limited to, appropriate media, bioreactor, temperature, pH and oxygen conditions that permit identification of resistance or product production. An appropriate, or effective, medium refers to any medium in which a strain of the present invention, when cultured, is capable of growing and/or expressing the nucleic acid molecule with which the strain has been transformed. Such a medium is typically an aqueous medium comprising assimilable carbon, nitrogen and phosphate sources, as well as appropriate salts, minerals, metals and other nutrients, such as vitamins. The medium may comprise complex nutrients or may be a defined minimal medium.

Strains of the present invention can be cultured in conventional fermentation bioreactors, which include, but are not limited to, batch, fed-batch, cell recycle, and continuous fermentors. Further, culturing can be conducted in outdoor open ponds. Culturing can also be conducted in shake flasks, test tubes, microtiter dishes, and petri plates. Culturing is carried out at a temperature, pH and oxygen content appropriate for the recombinant cell. Such culturing conditions are well within the expertise of one of ordinary skill in the art.

The use of a dominant selectable marker, as in the present invention, is considered to have significant advantages over the use of wild-type homologous genes to complement auxotrophic mutant strains which have been used as selectable marker systems for some green algae. For example, Kindle et al., 1989. *Journal of Cell Biology*, 109, 2589–2601, discusses the transformation of a nitrate reductase deficient mutant of *Chlamydomonas reinhardtii* with a gene encoding nitrate reductase. One disadvantage associated with such systems is that they require production of an appropriate auxotrophic strain prior to transformation and production of auxotrophic mutant strains can be particularly difficult in diploid organisms, such as diatoms. Additionally, auxotrophic strains can spontaneously revert to wild-type strains.

Compounds to which selectable markers confer resistance when expressed in algae can include metabolic inhibitors (i.e., compounds that inhibit algal metabolism). Examples of such compounds include antibiotics, fungicides, algicides, and herbicides. Functionally, such compounds are toxic to the cell or otherwise inhibit metabolism by functioning as protein or nucleic acid binding agents. For example, such compounds can inhibit translation, transcription, enzyme function, cell growth, cell division and/or microtubule formation.

Appropriate concentrations of such compounds to identify differences in sensitivity between transformed and non-transformed algae can be determined experimentally using techniques known to those skilled in the art (see e.g. Sambrook et al., *Molecular Cloning: A Laboratory Manual*, Cold Spring Harbor Labs Press, 1989).

Dominant selectable markers suitable for use in the present invention can be selected from any known or subsequently identified selectable markers, including markers derived from fungal and bacterial sources. Preferred dominant selectable markers can be selected from those identified in Table 1. In a more preferred embodiment, the dominant selectable marker is neomycin phosphotransferase.

TABLE 1

| COMPOUND | DOMINANT SELECTABLE MARKER |
| --- | --- |
| G418 | neomycin phosphotransferase |
| kanamycin | neomycin phosphotransferase |
| neomycin | neomycin phosphotransferase |
| chloramphenicol | chloramphenicol acetyltransferase |
| hygromycin B | hygromycin B phosphotransferase |
| bleomycin | bleomycin binding protein |
| phleomycin | bleomycin binding protein |
| phosphinothricin | phosphinothricin acetyltransferase |
| bialaphos | phosphinothricin acetyltransferase |

TABLE 1-continued

| COMPOUND | DOMINANT SELECTABLE MARKER |
|---|---|
| streptomycin | streptomycin phosphotransferase |
| bromoxynil | bromoxynil nitrilase |
| glyphosate | resistant forms of 5-enolpyruvylshikimate-3-phosphate synthase |
| emetine | resistant forms of ribosomal protein S14 |
| cryptopleurine | resistant forms of ribosomal orotein S14 |
| sulfonylurea | resistant forms of acetolactate synthase |
| imidazolinone | resistant forms of acetolactate synthase |
| streptomycin | resistant forms of 16S ribosomal RNA |
| spectinomycin | resistant forms of 16S ribosomal RNA |
| erythromycin | resistant forms of 23S ribosomal RNA |
| methyl benzimidazole | resistant forms of tubulin gene |

In a further embodiment, the present invention includes a recombinant molecule including a nucleic acid molecule (e.g., a gene encoding a selectable marker, a gene encoding a product) operatively linked to an algal regulatory control sequence. As used herein, the term operatively linked refers to joining a nucleic acid molecule to an algal regulatory control sequence in a manner such that the nucleic acid molecule is able to be expressed as an RNA molecule and/or a protein when the recombinant molecule is transformed into an alga. Suitable regulatory control sequences include promoters, operators, repressors, enhancers, transcription termination sequences, sequences that regulate translation, and other regulatory control sequences that are compatible with the recombinant cell and that control the expression of nucleic acid molecules of the present invention. Preferred regulatory control sequences include transcription control sequences that are able to control or effect the initiation, elongation, and/or termination of transcription. Depending on the application, regulatory control sequences can be used that effect inducible or constitutive expression. It is to be noted that regulatory control sequences can be found in a variety of locations, including in 5' untranslated regions (i.e. regions upstream from the coding region) and 3' untranslated regions (i.e. regions downstream from the coding region), as well as in coding regions. Algal regulatory control sequences can be of nuclear, viral, extrachromosomal, mitochondrial, or chloroplastic origin.

Suitable regulatory control sequences include those naturally associated with the nucleic acid molecule to be expressed (if the nucleic acid molecule is derived from algae) or regulatory control sequences not naturally associated with the nucleic acid molecule to be expressed. The latter regulatory control sequences can be a sequence that controls expression of another gene within the same algal species (i.e., homologous to the alga) or can be derived from a different species (i.e., heterologous to the alga) and particularly from a different algal species, the regulatory control sequence being capable of controlling expression in the algal species to be transformed. To determine whether a putative regulatory control sequence is suitable, that putative regulatory control sequence is linked to a nucleic acid molecule that preferably encodes a protein that produces an easily detectable signal. That construction is introduced into an alga by standard techniques and expression thereof is monitored. For example, if the nucleic acid molecule encodes a dominant selectable marker, the alga is tested for the ability to grow in the presence of a compound for which the marker provides resistance.

In a preferred embodiment, the regulatory control sequence is derived from a chlorophyll C-containing alga of a class selected from the group consisting of Bacillariophyceae, Chrysophyceae, Phaeophyceae, Xanthophyceae, Raphidophyceae, Prymnesiophyceae and Cryptophyceae. In preferred embodiments, regulatory control sequences are derived from a diatom, particularly from Cyclotella, and more particularly from *Cyclotella cryptica*. In embodiments in which the regulatory control sequence is derived from *Cyclotella cryptica*, the alga being transformed is preferably selected from the group consisting of *Cyclotella cryptica* and *Navicula saprophila*.

In a further preferred embodiment, regulatory control sequences comprise *C. cryptica* acetyl-CoA carboxylase regulatory control sequences. Such regulatory control sequences can be selected from the group consisting of a *C. cryptica* acetyl-CoA carboxylase 5'-untranslated regulatory control sequence, a *C. cryptica* acetyl-CoA carboxylase 3'-untranslated regulatory control sequence, and combinations thereof. 5'-untranslated regulatory control sequences include transcription and translation initiation signals, and 3'-untranslated regulatory control sequences include transcription and translation termination signals. Further, such regulatory control sequences can be selected from the group consisting of a nucleic acid molecule comprising about 816 nucleotides immediately upstream from (5' from) the translation initiation site of the *C. cryptica* acetyl-CoA carboxylase gene, a nucleic acid molecule comprising about 445 nucleotides immediately upstream from (5' from) the translation initiation site of the *C. cryptica* acetyl-CoA carboxylase gene, a nucleic acid molecule comprising about 594 nucleotides immediately downstream from (3' from) the translation termination site of the *C. cryptica* acetyl-CoA carboxylase gene, and combinations thereof. The foregoing regulatory control sequences include the DNA sequences represented by SEQ ID NO:1, SEQ ID NO:2, and/or SEQ ID NO:3, as well as portions thereof capable of affecting the regulatory control functions of the sequences in SEQ ID NO:1, SEQ ID NO:2, and SEQ ID NO:3. SEQ ID NO:1 represents a DNA sequence about 445 nucleotides immediately upstream from the translation initiation site of the *C. cryptica* acetyl-CoA carboxylase gene. SEQ ID NO:2 represents a DNA sequence about 816 nucleotides immediately upstream from the translation initiation site of the *C. cryptica* acetyl-CoA carboxylase gene. SEQ ID NO:3 represents a DNA sequence about 594 nucleotides immediately downstream from the translation termination site of the *C. cryptica* acetyl-CoA carboxylase gene.

Portions of the foregoing sequences capable of effecting the regulatory control functions of the sequences in SEQ ID NO:1, SEQ ID NO:2, and SEQ ID NO:3 can be homologues of such sequences which include sequences having deletions, additions and/or substitutions of bases from the identified sequences but that are sufficiently similar to those sequences to effect the regulatory control functions of those sequences. Such homologues preferably include sequences having at least about 75% identity with one of the SEQ ID listings in the domain encoding a regulatory function, more preferably at least about 85% identity therewith, and most preferably at least about 95% identity therewith. Such homologues can be identified as follows. A putative homologue sequence can be substituted in place of one of the three sequences identified in the SEQ ID listings in an expression system in which the replaced sequence is tested for the ability to effectively regulate gene expression in a manner similar to the SEQ ID listing in question. The ability of a putative homologue to regulate gene expression is monitored by, for example, detection of a dominant or colorimetric marker encoded by a nucleic acid molecule operatively linked to the putative homologue.

As discussed in detail above, a method of the present invention involves introducing a recombinant molecule comprising a nucleic acid molecule encoding a dominant selectable marker operatively linked to an algal regulatory control sequence into a chlorophyll C-containing alga. The various components of recombinant molecules of the present invention have been discussed in detail above. Examples of recombinant molecules are discussed in the Examples Section and include the recombinant molecules identified as pACCNPT10, pACCNPT4.8, and pACCNPT5.1. These recombinant molecules include the DNA sequences represented by SEQ ID NO:4, SEQ ID NO:6 and SEQ ID NO:8, respectively. These recombinant molecules include nucleic acid molecules encoding neomycin phosphotransferase II (SEQ ID NO:5, SEQ ID NO:7 and SEQ ID NO:9, respectively) operatively linked to certain *Cyclotella cryptica* regulatory control sequences. Further examples of recombinant molecules include homologues of pACCNPT10, pACCNPT5.1 and pACCNPT4.8, which include molecules having deletions, additions and/or substitutions of bases from the sequences of pACCNPT10, pACCNPT5.1, and pACCNT4.8 but are sufficiently similar to those sequences to effect the functions of those sequences. Such homologues preferably include sequences having at least about 75% identity with one of pACCNPT10, pACCNPT5.1, and pACCNT4.8 in functional domains, more preferably at least about 85% identity therewith, and most preferably at least about 95% identity therewith.

Recombinant molecules of the present invention used to transform chlorophyll C-containing algae can also include a nucleic acid molecule encoding a product which is operatively linked to an algal regulatory control sequence such that the product is produced by the alga. As used herein, a product can include any compound or composition which has any research, commercial or industrial utility. The product can be an RNA molecule or a protein. An RNA molecule can function, for example, as an antisense molecule, a triple helix former, a ribozyme, or an RNA drug. A protein can be the final form of a compound having research, commercial or industrial utility or can be an enzyme that has a desired function, such as to effect, alone or in combination with other compounds, synthesis of a desired compound. An enzyme, for example, can be involved in the synthesis of a compound such as a vitamin, amino acid, lipid, fatty acid, organic acid, pigment, hormone or other growth factor. Alternatively, a product can be involved in the uptake or degradation of compounds such as in bioremediation applications or the uptake of carbon dioxide. Production of products can be accomplished by culturing strains transformed with a nucleic acid molecule encoding a product under conditions effective to produce a product as described above.

A product can either be a product that is naturally produced by the alga ("native") or that is not naturally produced by the alga except through transformation ("non-native"). In the case of the product being native to the alga, the result of transformation can be to increase the expression of a molecule already produced by the alga by introducing into the alga extra copies of DNA which encode the molecule. Native products can also be used to decrease expression of a molecule. For example, insertion of extra copies of a homologous gene can lead to suppression of the native gene (transgene cosuppression). Further, overexpression of one protein can lead to reduction of another due to feedback inhibition, or a homologous gene can be used for random insertional mutagenesis to inactivate another homologous gene. Products not naturally produced by algae can include, but are not limited to, a modified version of a native product, a modified or natural version of a product naturally produced by another organism or an antisense product.

A preferred product of the present invention is acetyl-CoA carboxylase. Algae can be transformed with a gene encoding acetyl-CoA carboxylase ("ACCase") which is a key enzyme in the lipid biosynthetic pathway. Such algae may be able to overproduce lipids and, as such, would be useful in the production of the alternative fuel source known as "biodiesel". Biodiesel is produced by a simple transesterification process that converts glycerolipids into methyl or ethyl esters of fatty acids, along with glycerol as a byproduct. Biodiesel is believed to have a number of advantages over petroleum-based fuels. Biodiesel is a cleaner burning fuel than conventional diesel and has a naturally low concentration of sulfur, leading to reduced production of sulfur oxides and particulates during combustion.

It should be noted that the embodiments of the present invention discussed above of methods to transform chlorophyll C-containing algae with recombinant molecules, including nucleic acid molecules encoding a product and encoding a dominant selectable marker, can be accomplished by various methods. One such method is transformation with a single recombinant molecule with nucleic acid molecules encoding both a product and a dominant selectable marker. Alternatively, transformation can be accomplished by use of two recombinant molecules, one including a nucleic acid molecule encoding a product and one including a nucleic acid molecule encoding a dominant selectable marker ("co-transformation").

A further embodiment of the present invention includes a recombinant chlorophyll C-containing algal strain. The present disclosure describes a variety of techniques and methods for successfully producing recombinant chlorophyll C-containing algae and a variety of different embodiments thereof. Transformation of algae as described herein can be accomplished by introducing one or more recombinant molecules having one or more nucleic acid molecules into an algal cell by a variety of known techniques for transforming cells. For example, the step of introducing the recombinant molecule can include microprojectile bombardment, protoplast fusion, electroporation, microinjection, agitation with silicon carbide whiskers and agitation with glass beads.

In one embodiment of the present invention, once an algal cell is transformed with a recombinant molecule of the present invention, the recombinant molecule is integrated into the algal cell genome. A significant advantage of integration is that the nucleic acid molecule is stably maintained in the cell. The recombinant molecule can be integrated into the nuclear genome of the algal strain, into a chloroplast genome, and/or into a mitochondrial genome of the said algal strain. Further, the integration can be random or targeted. Targeted integration can be used to accomplish gene replacement.

One advantage of the transformation method of the present invention is that stable algal transformants are produced. Such algae are capable of maintaining the recombinant molecule when cultured on a non-selective medium. Maintenance of a recombinant molecule can be evaluated by culturing the transformed alga on non-selective media (i.e., in the absence of the selective compound that was used to select transformants expressing the corresponding dominant selectable marker) conducive to algal growth and/or maintenance for a given time and then evaluating the ability of the alga to grow in the presence of the selective compound at a concentration of the selective compound which would inhibit growth of non-transformed algae. Suitable protocols for evaluating stability are provided in the Example section. Preferably, the transformed algae are capable of maintaining the recombinant molecule when cultured on a non-selective medium for at least about eight months.

A further embodiment of the invention is a chimeric molecule comprising one or more regulatory control sequences derived from one or more chlorophyll C-containing algae operatively linked to a nucleic acid molecule that encodes a selectable marker, an RNA molecule or a protein. The nucleic acid molecule does not naturally occur in association with (i.e., is not naturally regulated by one or more of) the regulatory control sequences. For example, the nucleic acid molecule can be derived from a different organism than the one or more regulatory control sequences or it can be from the same organism, but is not naturally associated with the regulatory control sequences. The chimeric gene is particularly useful to modify microorganisms, including algae and in particular, chlorophyll C-containing algae. The regulatory control sequences in the chimeric molecule are as broadly described above in relation to other embodiments of the present invention.

The chimeric molecule can also include a nucleic acid molecule encoding a dominant selectable marker operatively linked to one or more regulatory control sequences. The dominant selectable marker suitable for use in the chimeric molecule and regulatory control sequences suitable for use in conjunction with the dominant selectable marker are those broadly described above in conjunction with other embodiments of the present invention.

A further embodiment of the present invention includes a method to produce a recombinant chlorophyll C-containing alga in which a host cell is transformed with a nucleic acid molecule encoding a dominant selectable marker in such a manner that the marker is produced by the strain. The method includes culturing the transformed strain in the presence of a compound that is toxic to an alga not transformed by the marker nucleic acid molecule and to which the dominant selectable marker provides resistance. The method further includes isolating from the culture an algal strain that is capable of growing in the presence of the compound. The steps of culturing and isolating can be accomplished by standard procedures known to those skilled in the art. The dominant selectable marker and compound for use in the present invention are as discussed above in other embodiments of the invention.

In a further embodiment, the present invention includes a method to transform a chlorophyll C-containing algal strain which includes introducing into the strain a recombinant molecule. The recombinant molecule includes a nucleic acid molecule operatively linked to a regulatory control sequence such that the nucleic acid molecule is transcribed in the strain. The recombinant molecule in this method can be a nucleic acid molecule encoding a selectable marker and/or a product capable of being expressed in the strain. The marker is selected from the group consisting of a heterologous protein capable of conferring resistance to a compound to which the strain otherwise exhibits sensitivity and a homologous modified protein capable of conferring resistance to a compound to which the strain otherwise exhibits sensitivity. In other embodiments, the compound referred to above is as broadly described above with regard to other embodiments of the present invention.

A further embodiment of the present invention includes a method to transform a chlorophyll C-containing alga which includes introducing a recombinant vector into a chlorophyll C-containing alga. The recombinant vector encodes a dominant selectable marker and/or a product and is introduced in such a manner that the marker and/or product is produced by the alga. It should be noted that in this embodiment of the present invention, it is not necessary that the recombinant vector being introduced into the chlorophyll C-containing alga include regulatory control sequences. It is possible that recombinant vectors encoding dominant selectable markers and/or proteins can be introduced into a host cell genome in positions such that a naturally occurring homologous regulatory control sequence can regulate expression of the nucleic acid molecule in the recombinant vector. The dominant selectable marker and/or product in this embodiment of the present invention is as broadly described above with regard to other embodiments of the invention.

The following examples and test results are provided for the purposes of illustration and are not intended to limit the scope of the invention.

EXAMPLES

Example 1

This example describes the production of recombinant molecule pACCNPT10.

Construction of recombinant molecule pACCNPT10 is diagrammed in FIG. 1. Recombinant molecule pUCNPTb (depicted in FIG. 1-A), containing a functional neomycin phosphotransferase (nptII) gene flanked by BspHI restriction sites, was produced as follows. The nptII gene from $E.$ $coli$ transposon Tn5 was obtained via polymerase chain reaction (PCR) amplification using recombinant molecule pBI121 (available from Clontech, Palo Alto, Calif.) as the template. The forward primer (PRA8) had the sequence 5'-TTTCTCATGATTGAACAAG-3', also represented herein as SEQ ID NO:10, and the reverse primer (PRA9) had the sequence 5'-ACTCATGAAGCTTGCTCAGAAGAACTCG-3', also represented herein as SEQ ID NO:11. The reaction mixture contained 20 mM Tris-Cl (pH 8.2), 10 mM KCl, 6 mM $(NH_4)_2SO_4$, 2 mM $MgCl_2$, 0.1% Triton X-100, 10 µg/ml nuclease-free bovine serum albumin, 0.2 mM dNTPs, 0.6 µM of each primer, 8 ng template DNA, and 2.5 units of Pfu DNA polymerase (available from Stratagene, La Jolla, Calif.). The thermal profile was as follows: 94° C. for 4 min, (94° C. for 45 sec, 45° C. for 45 sec, 72° C. for 2 min)×30 cycles, 72° C. for 5 min. The 816-bp amplified fragment was ligated into SmaI-cut pUC118 (Vieira, J. and J. Messing. 1987. Production of single-stranded plasmid DNA. Meth. Enzymol. 153:3) to yield recombinant molecule pUCNPTb. Sequence analysis confirmed that the sequence of the cloned PCR fragment was correct. In pUCNPTb, the nptII gene was inserted in frame with the 5' end of the β-galactosidase coding sequence present in pUC118, and consequently the functionality of the gene could be ascertained by growth of pUCNPTb-transformed $E. coli$ cells on LB plates containing 50 µg/ml kanamycin.

Recombinant molecule pACC1 (depicted in FIG. 1-B) contains the entire coding region of the ACCase gene from $C. cryptica$ T13L (Roessler, P. G. and J. B. Ohlrogge. 1993.

Cloning and characterization of the gene that encodes acetyl-coenzyme A carboxylase in the alga *Cyclotella cryptica*. J. Biol. Chem. 268:19254–19259), along with 445 bp of upstream and 594 bp of downstream flanking sequence. This recombinant molecule was constructed by ligating a 7.8-kb SnaBI/SpeI fragment from a genomic lambda clone containing the entire ACCase gene into pBluescript KS+ (available from Stratagene, La Jolla, Calif.) that had been digested with SmaI and SpeI.

Recombinant molecule pACCNPT10 (depicted in FIG. 1-C) was produced by digesting pACC1 with NcoI, which cuts the recombinant molecule at the ACCase translation initiation site and 275 bp upstream from the ACCase stop codon. The 4.2-kb fragment (depicted in FIG. 1-D) was gel purified and ligated to a gel-purified 804-bp BspHI fragment (depicted in FIG. 1-E) from pUCNPTb containing the nptII gene. The resulting recombinant molecule, pACCNPT10, contains the nptII gene, operatively linked at the 5'-end by 445 nucleotides of the 5' untranslated region ("UT") sequence, including the ACCase promoter region fused precisely at the translation initiation codon, and followed by the final 275 bp of the ACCase coding region and 594 bp of the ACCase 3' untranslated region.

Example 2

This example describes the production of recombinant molecule pACCNPT4.8.

Figure 2:
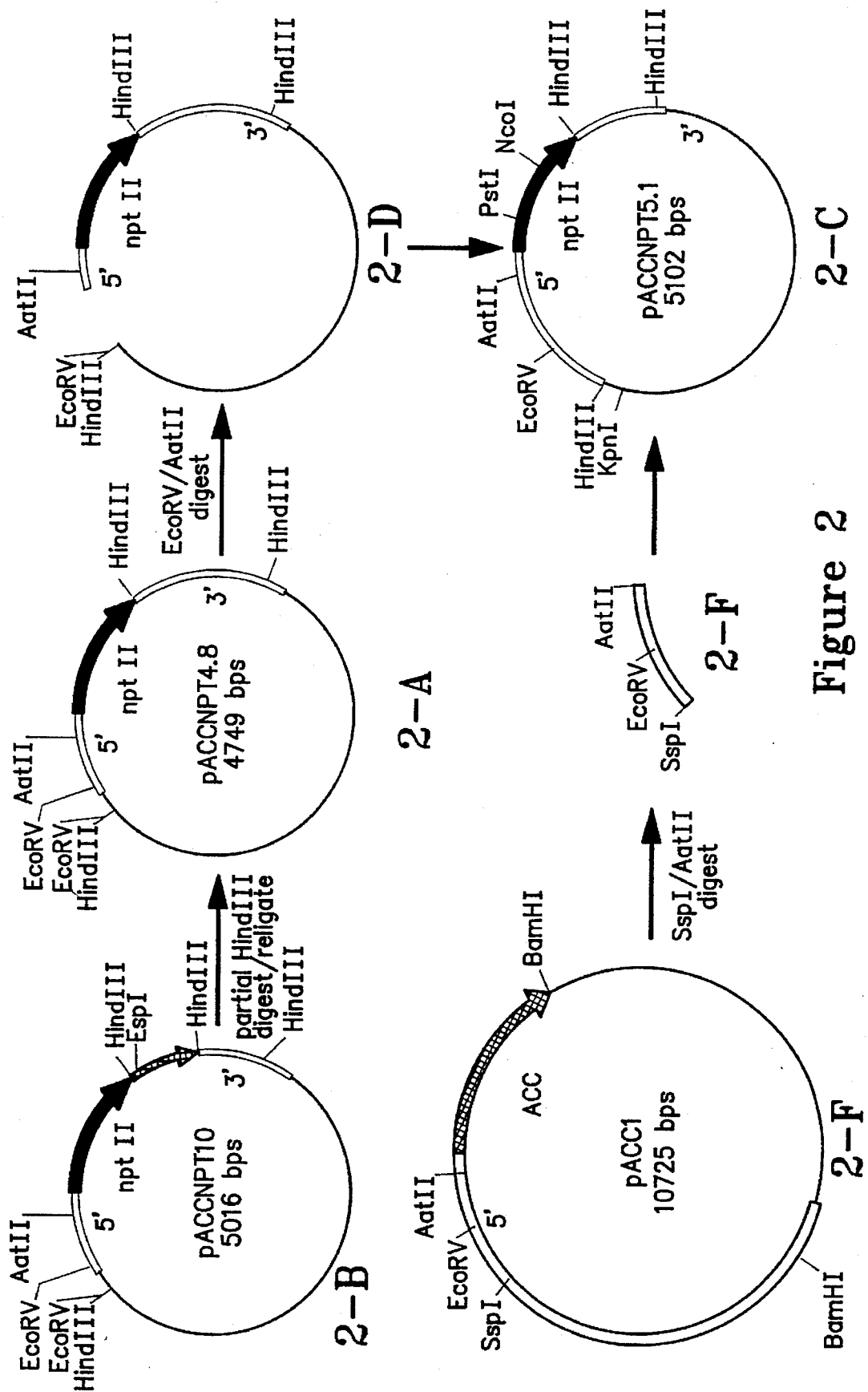
FIGS. 2A–2F illustrate construction of recombinant molecules pACCNPT4.8 and pACCNPT5.1.

Construction of recombinant molecule pACCNPT4.8 is diagrammed in FIG. 2. Recombinant molecule pACCNPT4.8 (depicted in FIG. 2-A) was produced from pACCNPT10 (depicted in FIG. 2-B) by removing all but 13 bp of the remaining ACCase coding sequence. pACCNPT10 was partially digested with HindIII, and one of the resulting fragments (4.7-kb) was gel purified and recircularized by incubation with T4 DNA ligase. Prior to transformation of *E. coli* cells with this recombinant molecule, the preparation was digested with EspI, which cuts pACCNPT10 only within the ACCase coding sequence. This step was included to reduce the chances of obtaining transformants containing unmodified pACCNPT10. Recombinant molecule pACCNPT4.8 contains the nptII gene operatively linked at the 5'-end by 445 nucleotides of the 5' UT sequence, including the ACCase promoter region fused precisely at the translation initiation codon, and followed by the final 13 bp of the ACCase coding region and 594 bp of the ACCase 3' untranslated region.

Example 3

This example describes the production of recombinant molecule pACCNPT5.1.

Construction of recombinant molecule pACCNPT5.1 (depicted in FIG. 2-C) is diagrammed in FIG. 2. pACCNPT5.1 was derived from pACCNPT4.8 and contains a longer ACCase 5' UT regulatory control region. pACCNPT4.8 (depicted in FIG. 2-A) was digested with EcoRV and AatII; an EcoRV site is within the original pBluescript KS+ polylinker, while the AatII site is within the ACCase promoter. In this process, 296 bp of the 5' end of the ACCase promoter was removed (depicted in FIG. 2-D). This fragment was replaced with a corresponding 670-bp SspI/AatII fragment (depicted in FIG. 2-E) isolated from recombinant molecule p2B4-9a (depicted in FIG. 2-F) (which contains more than 3 kilobases of sequence upstream from the ACCase coding sequence). This ligation resulted in recombinant molecule pACCNPT5.1 (depicted in FIG. 2-C), which contains 816 bp of the ACCase 5' UT regulatory control sequence operatively linked to the nptII gene, including the ACCase promoter region fused precisely at the translation initiation codon and followed by the final 13 bp of the ACCase coding region and 594 bp of the ACCase 3' untranslated region.

Example 4

This example describes the transformation of two strains of *Cyclotella cryptica* and one strain of *Navicula saprophila* with the recombinant molecules described in Examples 1–3 by microprojectile bombardment to introduce G418 resistance into the organisms. G418 is an aminoglycloside antibiotic purchased from SIGMA, St. Louis, Mo. Analysis of transformation of the specific strains is described below in Examples 5–8.

The strains and culture conditions are as follows. The centric diatom *C. cryptica* Reimann, Lewin, and Guillard strain T13L (Reimann, B. E. F., J. M. C. Lewin, and R. R. L. Guillard. 1963. *Cyclotella cryptica*, a new brackish-water diatom species. Phycologia 3:75–84) was obtained from the Provasoli-Guillard National Center for Culture of Marine Phytoplankton (West Boothbay Harbor, Me.). *C. cryptica* CYCLO1 and the pennate diatom *Navicula saprophila* NAVIC1 were obtained from the NREL Microalgal Culture Collection (Barclay, W., J. Johansen, P. Chelf, N. Nagle, P. Roessler, and P. Lemke. 1986. Microalgae Culture Collection 1986–1987, Solar Energy Research Institute, Golden, CO. SERI/SP-232-3079). Cells were grown axenically in artificial seawater medium (ASW; Brown, L. 1982. Production of axenic cultures of algae by an osmotic method. Phycologia 21:408–410) supplemented with 1.07 mM sodium silicate. In liquid culture, *C. cryptica* T13L was grown in 50% ASW, while *N. saprophila* NAVIC1 and *C. cryptica* CYCLO1 were grown in 10% ASW. Cultures were grown at 26° C. in Erlenmeyer flasks without agitation under a 16/8 hour light/dark cycle, with a light level of 50 $\mu$E·m$^-$2·sec$^{-1}$. For growth on solid media, all cultures were grown on 10% ASW supplemented with 20 mM glucose (ASWG) and 1% washed agar (available from Sigma, St. Louis, Mo.). All cultures were checked periodically for axenicity by culturing on YEG (1% yeast extract, 1% glucose) or on ASW supplemented with 0.5 g/l yeast extract, 0.5 g/l peptone, and 0.5 g/l tryptone.

The G418 sensitivity of each algal strain was determined empirically. Different numbers of wild-type cells were spread onto ASWG agar plates containing a range of G418 concentrations; combinations of cell density and G418 concentrations that resulted in no colonies appearing after 10 days were used for selection of transformants.

Recombinant molecules were introduced into the algal cells using the Dupont/Biorad PDS1000He microprojectile accelerator (available from BioRad Laboratories, Hercules, Calif.; Sanford, J. C., F. D. Smith, and J. A. Russell. 1993. Optimizing the biolistic process for different biological applications. Meth. Enzymol. 217:483–509). Prior to bombardment, the algal cells were collected by centrifugation and resuspended in growth medium. The cells were spread onto the center two-thirds of an ASWG agar plate (supplemented with 50 $\mu$g/ml ampicillin to reduce bacterial contamination during bombardment and recovery). Approximately $2 \times 10^7$ cells were used for each bombardment for the *C. cryptica* strains, and about $2 \times 10^8$ cells for *N. saprophila* NAVIC1. *C. cryptica* and *N. saprophila* NAVIC1 cells have cross-sectional areas of approximately 80 $\mu$m$^2$ and 15 $\mu$m$^2$, respectively. The goal was to spread the cells in an approximate monolayer on the agar plate prior to bombardment, thus a higher number of the smaller cells was needed. The plates were allowed to dry for at least 2 hours in a sterile transfer hood prior to bombardment.

Recombinant molecules were coated onto tungsten particles (0.5 μm particles available from Alfa Chemicals, Johnson Matthey, Danvers, Mass. or 1.0 μm M-10 particles available from DuPont, Wilmington, Del.) and the cells were bombarded with the particles as described in the PDS/1000He instruction manual. For most experiments, burst pressures of 1100 or 1300 psi were used. Cells were placed 8 cm from the stopping screen, and the distance between the burst disk holder and macroprojectile carrier was 0.5 cm. Ten microliters of the DNA/particle suspension, containing 3 mg tungsten and 0.8 to 1.0 μg recombinant molecule DNA, were used for each transformation. After bombardment, the plates were wrapped with PARAFILM®[1] and placed in a growth room for 2 days to allow the cells to recover and express the foreign gene. The cells were washed off of the plates with 5 ml of 10% ASW, transferred to 15 ml plastic centrifuge tubes, and collected by low-speed centrifugation. Following resuspension in a small volume of medium, the cells from each original plate were spread onto eight ASWG plates containing G418. G418-resistant colonies were typically seen within 7 to 10 days. The putative transformants were picked after 14 days and tested for continued growth on G418 plates and for the presence of the nptII gene and protein as described below.

[1] U.S. Trademark Registration No. 319,466, owned by Marathon PaperMills Company, Rothschild, Wis.

Example 5

Transformation of *C. cryptica* T13L with pACCNPT10.

*C. cryptica* T13L cells were bombarded with supercoiled recombinant molecule pACCNPT10 using burst pressures of 650, 900, or 1100 psi, and putative transformants were selected on ASWG plates containing 50 μg/ml G418. Under these conditions, several G418-resistant colonies apparently resulting from spontaneous mutations appeared on the untreated control plates. In subsequent experiments, transformants were selected on ASWG plates containing 100 μg/ml G418. Using the higher G418 concentration, no G418-resistant colonies appeared in over 1.2×10⁸ cells in control experiments (i.e., untreated cells or cells bombarded with pBluescript KS+).

Eleven G418-resistant isolates from this experiment were analyzed further, including one colony from the untreated control and ten putative transformants from the 900 and 1100 psi treatments. All colonies grew well when maintained on plates containing 50 μg/ml G418. To test for the presence of the foreign gene, DNA was isolated from wild-type *C. cryptica* T13L cells plus all eleven G418-resistant strains and analyzed on Southern blots.

Analysis for nptII DNA sequences.

DNA was isolated for Southern analysis by the glass bead/vortexing protocol as previously described (Jarvis, E. E., T. G. Dunahay, and L. M. Brown. 1992. DNA nucleoside composition and methylation in several species of microalgae. J. Phycol. 28:356–362). An additional precipitation with hexadecyltrimethylammonium bromide (CTAB) for removal of carbohydrates (Murray, H. G. and W. F. Thompson. 1980. Rapid isolation of high molecular weight plant DNA. Nucleic Acids Res. 3:4321–4325) was required for *C. cryptica* T13L and for *C. cryptica* CYCLO1 (described below in Example 7). Complete digestion of the genomic DNA from the twelve algal samples with PstI was achieved by overnight incubation and a high enzyme/DNA ratio. The DNA fragments were separated on 0.8% agarose gels and transferred to nylon membranes.

The nptII gene was detected using the Genius™ nonradioactive DNA detection system (available from Boehringer Mannheim Biochemicals, Indianapolis, Ind.) as per the manufacturer's instructions. The probe, which included the entire nptII coding region, was labeled with digoxigenin using the polymerase chain reaction and primers PRA8 and PRA9 described above, using the method of Lion and Haas (Lion, T. and O. A. Haas. 1990. Nonradioactive labeling of probe with digoxigenin by polymerase chain reaction. Anal. Biochem. 188:335–337). PstI cleaves pACCNPT10 into three fragments, two of which (631 bp and 734 bp) hybridize to the nptII probe. These two fragments were present in all ten G418-resistant colonies that had been bombarded by pACCNPT10. The two nptII-containing fragments were not present in DNA from wild-type cells or in the isolate from the untreated control. The presence of both fragments suggests the presence of at least one copy of the full-length nptII gene in all transformants. There also appeared to be differences in the numbers of copies of the nptII gene present in the different transformants. The presence of an additional 1.3-kb band in one sample indicated that integration of a partial or rearranged recombinant molecule fragment also occurred in that transformant.

Several of the transformants were analyzed further to obtain additional information about the integration patterns of the input DNA within the host genome. A Southern blot showing the hybridization of the nptII probe with algal DNA digested with BglII was conducted. BglII does not cut within the pACCNPT10 recombinant molecule. In each transformant tested, the nptII probe hybridized to a single high molecular weight band. This fact, plus the lack of hybridization to any bands that co-migrate with uncut pACCNPT10, confirms that the nptII DNA integrated into the host cell genome and was not replicating independently within the cell.

A Southern blot showing the hybridization of the nptII probe with algal DNA digested with NcoI was conducted. NcoI cuts at one site in pACCNPT10, within the nptII gene. If a single copy of the pACCNPT10 recombinant molecule integrates randomly within the genomic DNA, the expected hybridization signal would be two bands of varying sizes, depending upon where the recombinant molecule integrated relative to native NcoI sites within the genome. However, in all of the transformants tested in this experiment, the probe recognized a DNA fragment approximately 5-kb in length that co-migrated with a linearized pACCNPT10 recombinant molecule, as well as one or more other bands of varying sizes. This is apparently due to the integration of the recombinant molecule in the form of two or more tandem repeats, at one or more random sites within the host genome.

Analysis for NPTII Protein.

An assay for the presence of NPTII protein in putative transformants was performed by Western blotting. Cells were scraped from plates (approximately 10 μL packed cell volume) and placed in 50 μL of water in a microfuge tube. An equal volume of SDS 2× extraction buffer (125 mM Tris, 4% SDS, 20% glycerol, 10% β-mercaptoethanol) was added, and the sample was boiled for 5 min. Cell debris was removed by centrifugation, and 10 μL aliquots were electrophoresed on 6 to 18% SDS-polyacrylamide gels. The separated proteins were transferred to nitrocellulose, and NPTII protein was detected in all ten of the G418-resistant isolates using anti-NPTII primary antibodies (available from 5-Prime→3-Prime, Inc., Boulder, Colo.), and alkaline phosphatase-conjugated goat anti-rabbit IgG secondary antibodies.

All ten of the G418-resistant isolates that had been exposed to the NPTII-containing recombinant molecule produced a protein of approximately 30 kD that was recognized by the anti-NPTII antibody. This protein was not seen in the wild-type cells or in the G418-resistant colony isolated from the untreated control.

Stability of transformed phenotype.

The transformed *C. cryptica* T13L cells were routinely maintained on ASWG plus 50 or 100 µg/ml G418. To test the stability of the G418-resistant phenotype under non-selective conditions, five isolates (including a spontaneously-resistant isolate) were grown in liquid 50% ASW without G418. The cells were subcultured every 1 to 2 weeks. The cells were tested periodically for G418-resistance by transferring cells with a sterile inoculating loop onto 10% ASWG agar plus 100 µg·ml$^{-1}$ G418. The four transformants tested maintained their resistance for more than eight months, with no apparent loss in resistance to 100 µg/ml G418. The G418-resistant isolate from the untreated control gradually lost the ability to grow in the presence of G418.

Example 6

This example summarizes a number of experiments using either recombinant molecule pACCNPT10 or recombinant molecule pACCNPT5.1 to transform *C. cryptica* T13L to confirm initial transformation results and to test transformation efficiencies mediated by supercoiled recombinant molecules or recombinant molecules linearized by digestion with KpnI. The results of these experiments are summarized in Table 2.

TABLE 2

Transformation of *C. cryptica* T13L with pACCNPT10 and pACCNPT5.1

| Expt. # | plasmid | form of input DNA | # plates treated | #G418-resistant colonies | ave. # transf. per 3 × 10$^7$ cells |
|---|---|---|---|---|---|
| III | pACCNPT10 | supercoiled | 2 | 19 | 8.5 |
| III | pACCNPT5.1 | supercoiled | 2 | 9 | 4.5 |
| III | pBluescript | supercoiled | 1 | 0 | 0 |
| III | no plasmid | — | 1 | 0 | 0 |
| V | pACCNPT5.1 | supercoiled | 6 | 4 | 0.7 |
| V | pACCNPT5.1 | linear | 6 | 13 | 2.1 |
| V | pBluescript | supercoiled | 1 | 0 | 0 |
| IX | pACCNPT10 | linear | 1 | 2 | 2.0 |
| IX | pACCNPT5.1 | linear | 1 | 3 | 3.0 |
| X | pACCNPT10 | linear | 3 | 5 | 1.7 |
| XI | pACCNPT10 | supercoiled | 3 | 6 | 2.0 |
| XI | pACCNPT10 | linear | 3 | 2 | 0.7 |
| XI | no plasmid | — | 1 | 0 | 0 |
| XII | pACCNPT5.1 | supercoiled | 2 | 6 | 3 |

G418-resistant *C. cryptica* T13L colonies were obtained reproducibly using both pACCNPT10 and pACCNPT5.1. The average number of colonies obtained per bombarded plate (approximately 3×10$^7$ cells) ranged from less than one to about eight, and was not affected significantly by whether input DNA was supercoiled or linearized. Of all colonies that demonstrated continued growth in the presence of 100 µg/ml G418, 29 were chosen at random and tested for the presence of NPTII protein by Western blotting. All contained the NPTII protein.

Example 7

This example demonstrates transformation of another strain of *C. cryptica*, designated *C. cryptica* CYCLO1, with pACCNPT10 and pACCNPT5.1.

*C. cryptica* CYCLO1 cells were bombarded with pACCNPT10 or pACCNPT5.1 as described for *C. cryptica* T13L, except that transformants were selected on ASWG containing 50 µg/ml G418. Under these conditions, no spontaneously resistant isolates of *C. cryptica* CYCLO1 were seen. After bombardment of *C. cryptica* CYCLO1 with the recombinant molecules, a total of 14 G418-resistant isolates were obtained. Production of NPTII protein by all 14-putative transformants was confirmed by Western blot analysis. Although the *C. cryptica* CYCLO1 transformants were selected on 50 µg/ml G418, the colonies demonstrated resistance to much higher G418 concentrations. All *C. cryptica* CYCLO1 transformants grew well on 10% ASWG containing 200 µg/ml G418, and four transformants were resistant to at least 1 mg/ml G418. The results of this experiment are provided in Table 3.

TABLE 3

| Expt. # | algal strain | G418 conc. used for selection | plasmid[1] | # plates | #G418-resistant isolates |
|---|---|---|---|---|---|
| III | CYCLOI | 50 µg/ml | pACCNPT10 | 2 | 2 |
| III | CYCLOI | 50 µg/ml | pACCNPT5.1 | 2 | 12 |
| III | CYCLOI | 50 µg/ml | control[2] | 2 | 0 |

[1]All plasmids used in these experiments were supercoiled.
[2]The control included one plate not exposed to plasmid, and one plate treated with pBluescript KS+.

DNA was isolated from several G418-resistant strains of *C. cryptica* CYCLO1 and analyzed by Southern blotting. All contained at least one copy of the nptII DNA. The integration pattern of the input DNA was more variable than was seen in *C. cryptica* T13L, showing fewer tandem repeats and an increased tendency to integrate the input DNA at multiple sites within the genome.

Example 8

This example shows that *C. cryptica* regulatory control sequences function in the distantly related diatom *N. saprophila*. *N. saprophila* NAVIC1 cells were bombarded with pACCNPT5.1 as described for *C. cryptica* T13L, except that transformants were selected on ASWG containing 25 µg/ml G418. After bombardment of *N. saprophila* NAVIC1 with the recombinant molecule, a total of 42 G418-resistant isolates were isolated after 14 days from five plates. Of 15 colonies picked at random, all tested positive for the presence of NPTII protein. The results of this experiment are provided in Table 4.

TABLE 4

| Expt. # | algal strain | G418 conc. used for selection | plasmid[1] | # plates | #G418-resistant isolates |
|---|---|---|---|---|---|
| VI | NAVICI | 25 µg/ml | pACCNPT5.1 | 5 | 42 |
| VI | NAVICI | 25 µg/ml | no plasmid | 1 | 0 |

DNA was isolated from several *N. saprophila* transformants and analyzed by Southern blotting. The data show that *N. saprophila* integrates the foreign recombinant molecule, but not necessarily in the form of tandem repeats.

Example 9

This example demonstrates the introduction of at least one additional copy of the *C. cryptica* acetyl-CoA carboxylase gene into *C. cryptica* T13L and *Navicula saprophila*.

C. cryptica T13L or N. saprophila cells were bombarded with tungsten microprojectiles coated with a mixture of plasmid pACCNPT5.1 and plasmid pACC1 (FIG. 1) which contains a full length copy of the acetyl-CoA carboxylase gene from C. cryptica T13L. Transformants were selected based on their ability to grow in the presence of G418 as described previously. These transformants were then screened for the presence of pACC1 sequences using the polymerase chain reaction. Several transformants were identified that contained pACC1 sequences integrated into the host cell genome. Further analysis by Southern blotting demonstrated that at least one isolate of each species contained one or more additional full length copies of the C. cryptica T13L acetyl-CoA carboxylase gene. This experiment confirms the possibility of using a chimeric selectable marker gene in cotransformation protocols to facilitate the introduction of a nonselectable gene that encodes a potentially useful protein into diatoms.

---

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 445 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: 5'UTR
        ( B ) LOCATION: 1..445

( x i ) SEQUENCE DESCRIPTION: SEQ ID NO:1:

```
GTAAGAAAAA  AATCGTAATT  TCAAATATAT  TACCAATTTT  ACTTTTGATA  TCGCAGCCCT       60
TGTTCCCCGA  TATGTATCTT  TCAACGTGCT  GACGTACGCC  CCTACGAGCC  GTTGATGGCC      120
GAAATCTTCG  TGGATGTGTA  TCGTAAAATT  ATAAATATG   AAAGTATGGT  AGGTGGTAGG      180
TACGGTATTG  TACGATACAT  CTGTCTTGTG  ATGCGTTCAT  TCGCCACTGG  CGTACTTCCA      240
TCAAAAACTC  ACCCAAAGGC  CCGCTCCTGC  CAGCCACGGT  CGTCTTTTGT  GGACGTCAAC      300
AACCTTCAAT  ATCGAGTTCG  TTGTGATTGA  CGCATCCTCT  CCGAATTGGC  ATTGCGTTGT      360
TGAACACTCT  TAACTTTCGG  CATTTCCTCA  CGATAGTCAT  AAATCAACTG  CACATCCTCG      420
TCGACTTTGA  AAACGACATC  AAACC                                               445
```

( 2 ) INFORMATION FOR SEQ ID NO:2:

( i ) SEQUENCE CHARACTERISTICS:
        ( A ) LENGTH: 816 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: 5'UTR
        ( B ) LOCATION: 1..816

( x i ) SEQUENCE DESCRIPTION: SEQ ID NO:2:

```
ATTGTTCAAG  GGCCACAATC  TGCCACAATG  AAAGCTGAAG  TGGAGGCCAA  GCGAATGTAG       60
TGACAGTTTT  GACACCATCC  TTGAAGTAAA  AACTATAGAC  GTACTCCAAG  AAGAAGAAGA      120
ACGAATTTGA  TTAAGTACGT  CACAGTGATG  TCATCCTGAA  GTATGCCTGG  CCATCGTTTC      180
CACTCTCCGC  GACGTTACGA  CTTCGTGTGT  CGGCATTTCG  TCAGTGGTTT  TGTGCTATAC      240
ATGACATCAT  CCAAAATCGT  CACAAAGATC  CAAAAGATAT  AAGAGGGAGG  TGGAGTTCGC      300
ATTGGATGTA  GAGGAGCTTC  CATAATAAAA  AAATATATCG  ATACAAGTAA  CATTTTCTAC      360
```

```
AACGACTTTA  CGTAAGAAAA  AAATCGTAAT  TTCAAATATA  TTACCAATTT  TACTTTTGAT    420

ATCGCAGCCC  TTGTTCCCCG  ATATGTATCT  TTCAACGTGC  TGACGTACGC  CCCTACGAGC    480

CGTTGATGGC  CGAAATCTTC  GTGGATGTGT  ATCGTAAAAT  TATAAAATAT  GAAAGTATGG    540

TAGGTGGTAG  GTACGGTATT  GTACGATACA  TCTGTCTTGT  GATGCGTTCA  TTCGCCACTG    600

GCGTACTTCC  ATCAAAAACT  CACCCAAAGG  CCCGCTCCTG  CCAGCCACGG  TCGTCTTTTG    660

TGGACGTCAA  CAACCTTCAA  TATCGAGTTC  GTTGTGATTG  ACGCATCCTC  TCCGAATTGG    720

CATTGCGTTG  TTGAACACTC  TTAACTTTCG  GCATTTCCTC  ACGATAGTCA  TAAATCAACT    780

GCACATCCTC  GTCGACTTTG  AAAACGACAT  CAAACC                                816
```

( 2 ) INFORMATION FOR SEQ ID NO:3:

( i ) SEQUENCE CHARACTERISTICS:
        ( A ) LENGTH: 594 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: 3'UTR
        ( B ) LOCATION: 1..594

( x i ) SEQUENCE DESCRIPTION: SEQ ID NO:3:

```
TAAAAAATAG  GGGGAAATAA  ACTGGTTTGA  TTCCAGTTTG  AATTTATCTA  TTTTTAGAAA     60

TGTAGCTCGG  TAATTCTTTA  CTTTTAGGAT  TGCTTTTCAT  TAGTGAAATG  TATTTGTTAG    120

GTCCAGGCCT  TACATCGTAC  TGTGAATATT  ACAATTTTTG  ACTTATTGT   AGGAGGGGAG    180

AGAACACCAA  ATATTGGTGA  CAGAATGAGC  CATTACATTA  CCACATCAGA  TTATGGTAGA    240

GAGTTGATTG  AATGTACTCT  CAAATATTTA  ACCCTCAAAT  ATTGACTATA  TTAAGAGTGC    300

ACTAACAGAT  GACCTATAGA  CCCCAAAAAT  TTCCTATCTA  CCGTATATCT  CTGAGCATAA    360

CCATTAACAC  GATTTTGATA  TGTGGTGAGA  ACTTTGATG   GGACAAATTT  TTGCCTATTG    420

AGTGACACAC  CAAAACCTTC  AGAAGAAGGT  AAGCTTTTG   AAGTATATTA  TCCGTTTAGT    480

CGAGAATCGC  TTAGTTTTCA  AAATATACGC  AGTTCAAAAG  TAGGGTGGGT  CTTATTATCC    540

GTGGGGTCTT  ATGCTCAGAG  ATATACGGTA  TTATGTTTTC  ATAGCTTCAC  TAGT          594
```

( 2 ) INFORMATION FOR SEQ ID NO:4:

( i ) SEQUENCE CHARACTERISTICS:
        ( A ) LENGTH: 2120 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        1.
        ( A ) NAME/KEY: 5'UTR
        ( B ) LOCATION: 1..445
        ( D ) OTHER INFORMATION: /label=ACCase
        2.
        ( A ) NAME/KEY: CDS
        ( B ) LOCATION: 446..1240
        ( D ) OTHER INFORMATION: /label=NPTII
        3.
        ( A ) NAME/KEY: Linker Sequence
        ( B ) LOCATION: 1241..1248
        4.
        ( A ) NAME/KEY: ACCase 3'coding region (in non-translatable
            reading frame)

5,661,017

(B) LOCATION: 1249..1526
5.
(A) NAME/KEY: 3'UTR
(B) LOCATION: 1527..2120
(D) OTHER INFORMATION: /label=ACCase (xi) SEQUENCE DESCRIPTION: SEQ ID NO:4:

| | | | | |
|---|---|---|---|---|
| GTAAGAAAAA AATCGTAATT TCAAATATAT TACCAATTTT ACTTTTGATA TCGCAGCCCT | | | | 60 |
| TGTTCCCCGA TATGTATCTT TCAACGTGCT GACGTACGCC CCTACGAGCC GTTGATGGCC | | | | 120 |
| GAAATCTTCG TGGATGTGTA TCGTAAAATT ATAAAATATG AAAGTATGGT AGGTGGTAGG | | | | 180 |
| TACGGTATTG TACGATACAT CTGTCTTGTG ATGCGTTCAT TCGCCACTGG CGTACTTCCA | | | | 240 |
| TCAAAAACTC ACCCAAAGGC CGCTCCTGC CAGCCACGGT CGTCTTTGT GGACGTCAAC | | | | 300 |
| AACCTTCAAT ATCGAGTTCG TTGTGATTGA CGCATCCTCT CCGAATTGGC ATTGCGTTGT | | | | 360 |
| TGAACACTCT TAACTTTCGG CATTTCCTCA CGATAGTCAT AAATCAACTG CACATCCTCG | | | | 420 |
| TCGACTTTGA AAACGACATC AAACC ATG ATT GAA CAA GAT GGA TTG CAC GCA | | | | 472 |

```
                                      Met Ile Glu Gln Asp Gly Leu His Ala
                                       1               5
GGT TCT CCG GCC GCT TGG GTG GAG AGG CTA TTC GGC TAT GAC TGG GCA         520
Gly Ser Pro Ala Ala Trp Val Glu Arg Leu Phe Gly Tyr Asp Trp Ala
 10              15                  20                  25

CAA CAG ACA ATC GGC TGC TCT GAT GCC GCC GTG TTC CGG CTG TCA GCG         568
Gln Gln Thr Ile Gly Cys Ser Asp Ala Ala Val Phe Arg Leu Ser Ala
                 30                  35                  40

CAG GGG CGC CCG GTT CTT TTT GTC AAG ACC GAC CTG TCC GGT GCC CTG         616
Gln Gly Arg Pro Val Leu Phe Val Lys Thr Asp Leu Ser Gly Ala Leu
             45                  50                  55

AAT GAA CTG CAG GAC GAG GCA GCG CGG CTA TCG TGG CTG GCC ACG ACG         664
Asn Glu Leu Gln Asp Glu Ala Ala Arg Leu Ser Trp Leu Ala Thr Thr
         60                  65                  70

GGC GTT CCT TGC GCA GCT GTG CTC GAC GTT GTC ACT GAA GCG GGA AGG         712
Gly Val Pro Cys Ala Ala Val Leu Asp Val Val Thr Glu Ala Gly Arg
     75                  80                  85

GAC TGG CTG CTA TTG GGC GAA GTG CCG GGG CAG GAT CTC CTG TCA TCT         760
Asp Trp Leu Leu Leu Gly Glu Val Pro Gly Gln Asp Leu Leu Ser Ser
 90                  95                 100                 105

CAC CTT GCT CCT GCC GAG AAA GTA TCC ATC ATG GCT GAT GCA ATG CGG         808
His Leu Ala Pro Ala Glu Lys Val Ser Ile Met Ala Asp Ala Met Arg
                110                 115                 120

CGG CTG CAT ACG CTT GAT CCG GCT ACC TGC CCA TTC GAC CAC CAA GCG         856
Arg Leu His Thr Leu Asp Pro Ala Thr Cys Pro Phe Asp His Gln Ala
            125                 130                 135

AAA CAT CGC ATC GAG CGA GCA CGT ACT CGG ATG GAA GCC GGT CTT GTC         904
Lys His Arg Ile Glu Arg Ala Arg Thr Arg Met Glu Ala Gly Leu Val
        140                 145                 150

GAT CAG GAT GAT CTG GAC GAA GAG CAT CAG GGG CTC GCG CCA GCC GAA         952
Asp Gln Asp Asp Leu Asp Glu Glu His Gln Gly Leu Ala Pro Ala Glu
    155                 160                 165

CTG TTC GCC AGG CTC AAG GCG CGC ATG CCC GAC GGC GAG GAT CTC GTC        1000
Leu Phe Ala Arg Leu Lys Ala Arg Met Pro Asp Gly Glu Asp Leu Val
170                 175                 180                 185

GTG ACC CAT GGC GAT GCC TGC TTG CCG AAT ATC ATG GTG GAA AAT GGC        1048
Val Thr His Gly Asp Ala Cys Leu Pro Asn Ile Met Val Glu Asn Gly
                190                 195                 200

CGC TTT TCT GGA TTC ATC GAC TGT GGC CGG CTG GGT GTG GCG GAC CGC        1096
Arg Phe Ser Gly Phe Ile Asp Cys Gly Arg Leu Gly Val Ala Asp Arg
            205                 210                 215

TAT CAG GAC ATA GCG TTG GCT ACC CGT GAT ATT GCT GAA GAG CTT GGC        1144
```

|       |       |       |       |       |       |       |       |       |       |       |       |       |       |       |       |       |
|---|---|---|---|---|---|---|---|---|---|---|---|---|---|---|---|---|
| Tyr | Gln | Asp | Ile | Ala | Leu | Ala | Thr | Arg | Asp | Ile | Ala | Glu | Leu | Gly | | |
|     |     | 220 |     |     |     |     | 225 |     |     |     |     | 230 |     |     | | |

| GGC | GAA | TGG | GCT | GAC | CGC | TTC | CTC | GTG | CTT | TAC | GGT | ATC | GCC | GCT | CCC | 1192 |
|---|---|---|---|---|---|---|---|---|---|---|---|---|---|---|---|---|
| Gly | Glu | Trp | Ala | Asp | Arg | Phe | Leu | Val | Leu | Tyr | Gly | Ile | Ala | Ala | Pro | |
| | 235 | | | | | 240 | | | | | 245 | | | | | |

| GAT | TCG | CAG | CGC | ATC | GCC | TTC | TAT | CGC | CTT | CTT | GAC | GAG | TTC | TTC | TGAGCAAG | 1247 |
|---|---|---|---|---|---|---|---|---|---|---|---|---|---|---|---|---|
| Asp | Ser | Gln | Arg | Ile | Ala | Phe | Tyr | Arg | Leu | Leu | Asp | Glu | Phe | Phe | | |
| 250 | | | | | 255 | | | | | 260 | | | | 265 | | |

| TCATGGGCTC | GCTCTCGTGA | ATACTTCTTT | TATCTTGCTA | AGCGCCGCAT | TTTTCAAGAC | 1307 |
|---|---|---|---|---|---|---|
| AACTATGTGT | TGCAAATCAC | TGCTGCTGAT | CCTTCGTTAG | ACTCTAAGGC | TGCTCTTGAG | 1367 |
| GTGTTGAAGA | ACATGTGCAC | TGCAGACTGG | GATGACAACA | AAGCCGTTCT | TGACTATTAT | 1427 |
| CTGTCCAGCG | ATGGAGACAT | CACAGCCAAG | ATTAGCGAGA | TGAAGAAGGC | AGCTATCAAG | 1487 |
| GCACAGATCG | AGCAGCTTCA | GAAAGCTTTG | GAGGGTTGAT | AAAAAATAGG | GGGAAATAAA | 1547 |
| CTGGTTTGAT | TCCAGTTTGA | ATTTATCTAT | TTTTAGAAAT | GTAGCTCGGT | AATTCTTTAC | 1607 |
| TTTTAGGATT | GCTTTTCATT | AGTGAAATGT | ATTTGTTAGG | TCCAGGCCTT | ACATCGTACT | 1667 |
| GTGAATATTA | CAATTTTTGA | CTTATTTGTA | GGAGGGGAGA | GAACACCAAA | TATTGGTGAC | 1727 |
| AGAATGAGCC | ATTACATTAC | CACATCAGAT | TATGGTAGAG | AGTTGATTGA | ATGTACTCTC | 1787 |
| AAATATTTAA | CCCTCAAATA | TTGACTATAT | TAAGAGTGCA | CTAACAGATG | ACCTATAGAC | 1847 |
| CCCAAAAATT | TCCTATCTAC | CGTATATCTC | TGAGCATAAC | CATTAACACG | ATTTTGATAT | 1907 |
| GTGGTGAGAA | CTTTTGATGG | GACAAATTTT | TGCCTATTGA | GTGACACACC | AAAACCTTCA | 1967 |
| GAAGAAGGTA | AGCTTTTTGA | AGTATATTAT | CCGTTTAGTC | GAGAATCGCT | TAGTTTTCAA | 2027 |
| AATATACGCA | GTTCAAAAGT | AGGGTGGGTC | TTATTATCCG | TGGGGTCTTA | TGCTCAGAGA | 2087 |
| TATACGGTAT | TATGTTTTCA | TAGCTTCACT | AGT | | | 2120 |

( 2 ) INFORMATION FOR SEQ ID NO:5:

( i ) SEQUENCE CHARACTERISTICS:
        ( A ) LENGTH: 264 amino acids
        ( B ) TYPE: amino acid
        ( D ) TOPOLOGY: linear ( i i ) MOLECULE TYPE: protein ( x i ) SEQUENCE DESCRIPTION: SEQ ID NO:5:

| Met | Ile | Glu | Gln | Asp | Gly | Leu | His | Ala | Gly | Ser | Pro | Ala | Ala | Trp | Val |
|---|---|---|---|---|---|---|---|---|---|---|---|---|---|---|---|
| 1 | | | | 5 | | | | | 10 | | | | | 15 | |

| Glu | Arg | Leu | Phe | Gly | Tyr | Asp | Trp | Ala | Gln | Gln | Thr | Ile | Gly | Cys | Ser |
|---|---|---|---|---|---|---|---|---|---|---|---|---|---|---|---|
| | | | 20 | | | | | 25 | | | | | 30 | | |

| Asp | Ala | Ala | Val | Phe | Arg | Leu | Ser | Ala | Gln | Gly | Arg | Pro | Val | Leu | Phe |
|---|---|---|---|---|---|---|---|---|---|---|---|---|---|---|---|
| | | 35 | | | | | 40 | | | | | 45 | | | |

| Val | Lys | Thr | Asp | Leu | Ser | Gly | Ala | Leu | Asn | Glu | Leu | Gln | Asp | Glu | Ala |
|---|---|---|---|---|---|---|---|---|---|---|---|---|---|---|---|
| | 50 | | | | | 55 | | | | | 60 | | | | |

| Ala | Arg | Leu | Ser | Trp | Leu | Ala | Thr | Thr | Gly | Val | Pro | Cys | Ala | Ala | Val |
|---|---|---|---|---|---|---|---|---|---|---|---|---|---|---|---|
| 65 | | | | | 70 | | | | | 75 | | | | | 80 |

| Leu | Asp | Val | Val | Thr | Glu | Ala | Gly | Arg | Asp | Trp | Leu | Leu | Leu | Gly | Glu |
|---|---|---|---|---|---|---|---|---|---|---|---|---|---|---|---|
| | | | | 85 | | | | | 90 | | | | | 95 | |

| Val | Pro | Gly | Gln | Asp | Leu | Leu | Ser | Ser | His | Leu | Ala | Pro | Ala | Glu | Lys |
|---|---|---|---|---|---|---|---|---|---|---|---|---|---|---|---|
| | | | 100 | | | | | 105 | | | | | 110 | | |

| Val | Ser | Ile | Met | Ala | Asp | Ala | Met | Arg | Arg | Leu | His | Thr | Leu | Asp | Pro |
|---|---|---|---|---|---|---|---|---|---|---|---|---|---|---|---|
| | | | 115 | | | | | 120 | | | | | 125 | | |

| Ala | Thr | Cys | Pro | Phe | Asp | His | Gln | Ala | Lys | His | Arg | Ile | Glu | Arg | Ala |
|---|---|---|---|---|---|---|---|---|---|---|---|---|---|---|---|
| | 130 | | | | | 135 | | | | | 140 | | | | |

| | | | | | | | | | | | | | | | |
|---|---|---|---|---|---|---|---|---|---|---|---|---|---|---|---|
|Arg|Thr|Arg|Met|Glu|Ala|Gly|Leu|Val|Asp|Gln|Asp|Asp|Leu|Asp|Glu|
|145| | | | |150| | | | |155| | | | |160|
|Glu|His|Gln|Gly|Leu|Ala|Pro|Ala|Glu|Leu|Phe|Ala|Arg|Leu|Lys|Ala|
| | | | |165| | | | |170| | | | |175| |
|Arg|Met|Pro|Asp|Gly|Glu|Asp|Leu|Val|Val|Thr|His|Gly|Asp|Ala|Cys|
| | | |180| | | | |185| | | | |190| | |
|Leu|Pro|Asn|Ile|Met|Val|Glu|Asn|Gly|Arg|Phe|Ser|Gly|Phe|Ile|Asp|
| | |195| | | | |200| | | | |205| | | |
|Cys|Gly|Arg|Leu|Gly|Val|Ala|Asp|Arg|Tyr|Gln|Asp|Ile|Ala|Leu|Ala|
| |210| | | | |215| | | | |220| | | | |
|Thr|Arg|Asp|Ile|Ala|Glu|Glu|Leu|Gly|Gly|Glu|Trp|Ala|Asp|Arg|Phe|
|225| | | | |230| | | | |235| | | | |240|
|Leu|Val|Leu|Tyr|Gly|Ile|Ala|Ala|Pro|Asp|Ser|Gln|Arg|Ile|Ala|Phe|
| | | | |245| | | | |250| | | | |255| |
|Tyr|Arg|Leu|Leu|Asp|Glu|Phe|Phe| | | | | | | | |
| | | | |260| | | | | | | | | | | |

( 2 ) INFORMATION FOR SEQ ID NO:6:

( i ) SEQUENCE CHARACTERISTICS:
        ( A ) LENGTH: 1853 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        1.
        ( A ) NAME/KEY: 5'UTR
        ( B ) LOCATION: 1..445
        ( D ) OTHER INFORMATION: /label=ACCase
        2.
        ( A ) NAME/KEY: CDS
        ( B ) LOCATION: 446..1240
        ( D ) OTHER INFORMATION: /label=NPTII
        3.
        ( A ) NAME/KEY: Linker Sequence
        ( B ) LOCATION: 1241..1243
        4.
        ( A ) NAME/KEY: ACCase 3'coding region (in non-translatable reading frame)
        ( B ) LOCATION: 1244..1259
        5.
        ( A ) NAME/KEY: 3'UTR
        ( B ) LOCATION: 1260..1853
        ( D ) OTHER INFORMATION: /label=ACCase ( x i ) SEQUENCE DESCRIPTION: SEQ ID NO:6:

```
GTAAGAAAAA AATCGTAATT TCAAATATAT TACCAATTTT ACTTTTGATA TCGCAGCCCT      60

TGTTCCCCGA TATGTATCTT TCAACGTGCT GACGTACGCC CCTACGAGCC GTTGATGGCC     120

GAAATCTTCG TGGATGTGTA TCGTAAAATT ATAAATATG  AAAGTATGGT AGGTGGTAGG     180

TACGGTATTG TACGATACAT CTGTCTTGTG ATGCGTTCAT TCGCCACTGG CGTACTTCCA     240

TCAAAAACTC ACCCAAAGGC CCGCTCCTGC CAGCCACGGT CGTCTTTTGT GGACGTCAAC     300

AACCTTCAAT ATCGAGTTCG TTGTGATTGA CGCATCCTCT CCGAATTGGC ATTGCGTTGT     360

TGAACACTCT TAACTTTCGG CATTTCCTCA CGATAGTCAT AAATCAACTG CACATCCTCG     420

TCGACTTTGA AAACGACATC AAACC ATG ATT GAA CAA GAT GGA TTG CAC GCA      472
                            Met Ile Glu Gln Asp Gly Leu His Ala
                             1               5
```

| | | | | | | | | | | | | | | | | |
|---|---|---|---|---|---|---|---|---|---|---|---|---|---|---|---|---|
|GGT|TCT|CCG|GCC|GCT|TGG|GTG|GAG|AGG|CTA|TTC|GGC|TAT|GAC|TGG|GCA|520|
|Gly|Ser|Pro|Ala|Ala|Trp|Val|Glu|Arg|Leu|Phe|Gly|Tyr|Asp|Trp|Ala| |
|10| | | | |15| | | | |20| | | | |25| |

-continued

| | | | | | | | | | | | | | | | | |
|---|---|---|---|---|---|---|---|---|---|---|---|---|---|---|---|---|
| CAA | CAG | ACA | ATC | GGC | TGC | TCT | GAT | GCC | GCC | GTG | TTC | CGG | CTG | TCA | GCG | 568 |
| Gln | Gln | Thr | Ile | Gly | Cys | Ser | Asp | Ala | Ala | Val | Phe | Arg | Leu | Ser | Ala | |
| | | | 30 | | | | | 35 | | | | | 40 | | | |
| CAG | GGG | CGC | CCG | GTT | CTT | TTT | GTC | AAG | ACC | GAC | CTG | TCC | GGT | GCC | CTG | 616 |
| Gln | Gly | Arg | Pro | Val | Leu | Phe | Val | Lys | Thr | Asp | Leu | Ser | Gly | Ala | Leu | |
| | | | 45 | | | | | 50 | | | | | 55 | | | |
| AAT | GAA | CTG | CAG | GAC | GAG | GCA | GCG | CGG | CTA | TCG | TGG | CTG | GCC | ACG | ACG | 664 |
| Asn | Glu | Leu | Gln | Asp | Glu | Ala | Ala | Arg | Leu | Ser | Trp | Leu | Ala | Thr | Thr | |
| | | 60 | | | | | 65 | | | | | 70 | | | | |
| GGC | GTT | CCT | TGC | GCA | GCT | GTG | CTC | GAC | GTT | GTC | ACT | GAA | GCG | GGA | AGG | 712 |
| Gly | Val | Pro | Cys | Ala | Ala | Val | Leu | Asp | Val | Val | Thr | Glu | Ala | Gly | Arg | |
| | 75 | | | | | 80 | | | | | 85 | | | | | |
| GAC | TGG | CTG | CTA | TTG | GGC | GAA | GTG | CCG | GGG | CAG | GAT | CTC | CTG | TCA | TCT | 760 |
| Asp | Trp | Leu | Leu | Leu | Gly | Glu | Val | Pro | Gly | Gln | Asp | Leu | Leu | Ser | Ser | |
| 90 | | | | | 95 | | | | | 100 | | | | | 105 | |
| CAC | CTT | GCT | CCT | GCC | GAG | AAA | GTA | TCC | ATC | ATG | GCT | GAT | GCA | ATG | CGG | 808 |
| His | Leu | Ala | Pro | Ala | Glu | Lys | Val | Ser | Ile | Met | Ala | Asp | Ala | Met | Arg | |
| | | | 110 | | | | | 115 | | | | | 120 | | | |
| CGG | CTG | CAT | ACG | CTT | GAT | CCG | GCT | ACC | TGC | CCA | TTC | GAC | CAC | CAA | GCG | 856 |
| Arg | Leu | His | Thr | Leu | Asp | Pro | Ala | Thr | Cys | Pro | Phe | Asp | His | Gln | Ala | |
| | | | 125 | | | | | 130 | | | | | 135 | | | |
| AAA | CAT | CGC | ATC | GAG | CGA | GCA | CGT | ACT | CGG | ATG | GAA | GCC | GGT | CTT | GTC | 904 |
| Lys | His | Arg | Ile | Glu | Arg | Ala | Arg | Thr | Arg | Met | Glu | Ala | Gly | Leu | Val | |
| | | 140 | | | | | 145 | | | | | 150 | | | | |
| GAT | CAG | GAT | GAT | CTG | GAC | GAA | GAG | CAT | CAG | GGG | CTC | GCG | CCA | GCC | GAA | 952 |
| Asp | Gln | Asp | Asp | Leu | Asp | Glu | Glu | His | Gln | Gly | Leu | Ala | Pro | Ala | Glu | |
| | 155 | | | | | 160 | | | | | 165 | | | | | |
| CTG | TTC | GCC | AGG | CTC | AAG | GCG | CGC | ATG | CCC | GAC | GGC | GAG | GAT | CTC | GTC | 1000 |
| Leu | Phe | Ala | Arg | Leu | Lys | Ala | Arg | Met | Pro | Asp | Gly | Glu | Asp | Leu | Val | |
| 170 | | | | | 175 | | | | | 180 | | | | | 185 | |
| GTG | ACC | CAT | GGC | GAT | GCC | TGC | TTG | CCG | AAT | ATC | ATG | GTG | GAA | AAT | GGC | 1048 |
| Val | Thr | His | Gly | Asp | Ala | Cys | Leu | Pro | Asn | Ile | Met | Val | Glu | Asn | Gly | |
| | | | 190 | | | | | 195 | | | | | 200 | | | |
| CGC | TTT | TCT | GGA | TTC | ATC | GAC | TGT | GGC | CGG | CTG | GGT | GTG | GCG | GAC | CGC | 1096 |
| Arg | Phe | Ser | Gly | Phe | Ile | Asp | Cys | Gly | Arg | Leu | Gly | Val | Ala | Asp | Arg | |
| | | | 205 | | | | | 210 | | | | | 215 | | | |
| TAT | CAG | GAC | ATA | GCG | TTG | GCT | ACC | CGT | GAT | ATT | GCT | GAA | GAG | CTT | GGC | 1144 |
| Tyr | Gln | Asp | Ile | Ala | Leu | Ala | Thr | Arg | Asp | Ile | Ala | Glu | Glu | Leu | Gly | |
| | | 220 | | | | | 225 | | | | | 230 | | | | |
| GGC | GAA | TGG | GCT | GAC | CGC | TTC | CTC | GTG | CTT | TAC | GGT | ATC | GCC | GCT | CCC | 1192 |
| Gly | Glu | Trp | Ala | Asp | Arg | Phe | Leu | Val | Leu | Tyr | Gly | Ile | Ala | Ala | Pro | |
| | 235 | | | | | 240 | | | | | 245 | | | | | |
| GAT | TCG | CAG | CGC | ATC | GCC | TTC | TAT | CGC | CTT | CTT | GAC | GAG | TTC | TTC | TGAGCAAG | 1247 |
| Asp | Ser | Gln | Arg | Ile | Ala | Phe | Tyr | Arg | Leu | Leu | Asp | Glu | Phe | Phe | | |
| 250 | | | | 255 | | | | | 260 | | | | | | | |

| | | | | |
|---|---|---|---|---|
| TTGGAGGGTT | GATAAAAAAT | AGGGGGAAAT | AAACTGGTTT | GATTCCAGTT | TGAATTTATC | 1307 |
| TATTTTTAGA | AATGTAGCTC | GGTAATTCTT | TACTTTTAGG | ATTGCTTTTC | ATTAGTGAAA | 1367 |
| TGTATTTGTT | AGGTCCAGGC | CTTACATCGT | ACTGTGAATA | TTACAATTTT | TGACTTATTT | 1427 |
| GTAGGAGGGG | AGAGAACACC | AAATATTGGT | GACAGAATGA | GCCATTACAT | TACCACATCA | 1487 |
| GATTATGGTA | GAGAGTTGAT | TGAATGTACT | CTCAAATATT | TAACCCTCAA | ATATTGACTA | 1547 |
| TATTAAGAGT | GCACTAACAG | ATGACCTATA | GACCCCAAAA | ATTTCCTATC | TACCGTATAT | 1607 |
| CTCTGAGCAT | AACCATTAAC | ACGATTTTGA | TATGTGGTGA | GAACTTTTGA | TGGGACAAAT | 1667 |
| TTTTGCCTAT | TGAGTGACAC | ACCAAAACCT | TCAGAAGAAG | GTAAGCTTTT | TGAAGTATAT | 1727 |
| TATCCGTTTA | GTCGAGAATC | GCTTAGTTTT | CAAAATATAC | GCAGTTCAAA | AGTAGGGTGG | 1787 |
| GTCTTATTAT | CCGTGGGGTC | TTATGCTCAG | AGATATACGG | TATTATGTTT | TCATAGCTTC | 1847 |

-continued

ACTAGT                                                                                                          1853

( 2 ) INFORMATION FOR SEQ ID NO:7:

( i ) SEQUENCE CHARACTERISTICS:
        ( A ) LENGTH: 264 amino acids
        ( B ) TYPE: amino acid
        ( D ) TOPOLOGY: linear ( i i ) MOLECULE TYPE: protein ( x i ) SEQUENCE DESCRIPTION: SEQ ID NO:7:

```
Met  Ile  Glu  Gln  Asp  Gly  Leu  His  Ala  Gly  Ser  Pro  Ala  Ala  Trp  Val
 1                  5                        10                       15

Glu  Arg  Leu  Phe  Gly  Tyr  Asp  Trp  Ala  Gln  Gln  Thr  Ile  Gly  Cys  Ser
                20                       25                       30

Asp  Ala  Ala  Val  Phe  Arg  Leu  Ser  Ala  Gln  Gly  Arg  Pro  Val  Leu  Phe
            35                       40                       45

Val  Lys  Thr  Asp  Leu  Ser  Gly  Ala  Leu  Asn  Glu  Leu  Gln  Asp  Glu  Ala
     50                       55                       60

Ala  Arg  Leu  Ser  Trp  Leu  Ala  Thr  Thr  Gly  Val  Pro  Cys  Ala  Ala  Val
 65                       70                       75                       80

Leu  Asp  Val  Val  Thr  Glu  Ala  Gly  Arg  Asp  Trp  Leu  Leu  Leu  Gly  Glu
                     85                       90                       95

Val  Pro  Gly  Gln  Asp  Leu  Leu  Ser  Ser  His  Leu  Ala  Pro  Ala  Glu  Lys
               100                      105                      110

Val  Ser  Ile  Met  Ala  Asp  Ala  Met  Arg  Arg  Leu  His  Thr  Leu  Asp  Pro
          115                      120                      125

Ala  Thr  Cys  Pro  Phe  Asp  His  Gln  Ala  Lys  His  Arg  Ile  Glu  Arg  Ala
     130                      135                      140

Arg  Thr  Arg  Met  Glu  Ala  Gly  Leu  Val  Asp  Gln  Asp  Leu  Asp  Glu
145                      150                      155                      160

Glu  His  Gln  Gly  Leu  Ala  Pro  Ala  Glu  Leu  Phe  Ala  Arg  Leu  Lys  Ala
                    165                      170                      175

Arg  Met  Pro  Asp  Gly  Glu  Asp  Leu  Val  Val  Thr  His  Gly  Asp  Ala  Cys
               180                      185                      190

Leu  Pro  Asn  Ile  Met  Val  Glu  Asn  Gly  Arg  Phe  Ser  Gly  Phe  Ile  Asp
          195                      200                      205

Cys  Gly  Arg  Leu  Gly  Val  Ala  Asp  Arg  Tyr  Gln  Asp  Ile  Ala  Leu  Ala
     210                      215                      220

Thr  Arg  Asp  Ile  Ala  Glu  Glu  Leu  Gly  Gly  Glu  Trp  Ala  Asp  Arg  Phe
225                      230                      235                      240

Leu  Val  Leu  Tyr  Gly  Ile  Ala  Ala  Pro  Asp  Ser  Gln  Arg  Ile  Ala  Phe
                    245                      250                      255

Tyr  Arg  Leu  Leu  Asp  Glu  Phe  Phe
                    260
```

( 2 ) INFORMATION FOR SEQ ID NO:8:

( i ) SEQUENCE CHARACTERISTICS:
        ( A ) LENGTH: 2224 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        1.
        ( A ) NAME/KEY: 5'UTR
        ( B ) LOCATION: 1..816

(D) OTHER INFORMATION: /label=ACCase
2.
(A) NAME/KEY: CDS
(B) LOCATION: 817..1611
(D) OTHER INFORMATION: /label=NPTII
3.
(A) NAME/KEY: Linker Sequence
(B) LOCATION: 1612..1614
4.
(A) NAME/KEY: ACCase 3'coding region (in non-translatable reading frame)
(B) LOCATION: 1615..1630
5.
(A) NAME/KEY: 3'UTR
(B) LOCATION: 1631..2224
(D) OTHER INFORMATION: /label=ACCase (xi) SEQUENCE DESCRIPTION: SEQ ID NO:8:

```
ATTGTTCAAG GGCCACAATC TGCCACAATG AAAGCTGAAG TGGAGGCCAA GCGAATGTAG      60
TGACAGTTTT GACACCATCC TTGAAGTAAA AACTATAGAC GTACTCCAAG AAGAAGAAGA    120
ACGAATTTGA TTAAGTACGT CACAGTGATG TCATCCTGAA GTATGCCTGG CCATCGTTTC    180
CACTCTCCGC GACGTTACGA CTTCGTGTGT CGGCATTTCG TCAGTGGTTT TGTGCTATAC    240
ATGACATCAT CCAAAATCGT CACAAGATC CAAAGATAT AAGAGGGAGG TGGAGTTCGC      300
ATTGGATGTA GAGGAGCTTC CATAATAAAA AAATATATCG ATACAAGTAA CATTTTCTAC    360
AACGACTTTA CGTAAGAAAA AAATCGTAAT TTCAAATATA TTACCAATTT TACTTTTGAT    420
ATCGCAGCCC TTGTTCCCCG ATATGTATCT TTCAACGTGC TGACGTACGC CCCTACGAGC    480
CGTTGATGGC CGAAATCTTC GTGGATGTGT ATCGTAAAAT TATAAAATAT GAAAGTATGG    540
TAGGTGGTAG GTACGGTATT GTACGATACA TCTGTCTTGT GATGCGTTCA TTCGCCACTG    600
GCGTACTTCC ATCAAAAACT CACCCAAAGG CCCGCTCCTG CCAGCCACGG TCGTCTTTTG    660
TGGACGTCAA CAACCTTCAA TATCGAGTTC GTTGTGATTG ACGCATCCTC TCCGAATTGG    720
CATTGCGTTG TTGAACACTC TTAACTTTCG GCATTTCCTC ACGATAGTCA TAAATCAACT    780
GCACATCCTC GTCGACTTTG AAAACGACAT CAAACC ATG ATT GAA CAA GAT GGA      834
                                        Met Ile Glu Gln Asp Gly
                                         1              5
TTG CAC GCA GGT TCT CCG GCC GCT TGG GTG GAG AGG CTA TTC GGC TAT      882
Leu His Ala Gly Ser Pro Ala Ala Trp Val Glu Arg Leu Phe Gly Tyr
         10                  15                  20
GAC TGG GCA CAA CAG ACA ATC GGC TGC TCT GAT GCC GCC GTG TTC CGG      930
Asp Trp Ala Gln Gln Thr Ile Gly Cys Ser Asp Ala Ala Val Phe Arg
             25                  30                  35
CTG TCA GCG CAG GGG CGC CCG GTT CTT TTT GTC AAG ACC GAC CTG TCC      978
Leu Ser Ala Gln Gly Arg Pro Val Leu Phe Val Lys Thr Asp Leu Ser
         40                  45                  50
GGT GCC CTG AAT GAA CTG CAG GAC GAG GCA GCG CGG CTA TCG TGG CTG     1026
Gly Ala Leu Asn Glu Leu Gln Asp Glu Ala Ala Arg Leu Ser Trp Leu
 55                  60                  65                  70
GCC ACG ACG GGC GTT CCT TGC GCA GCT GTG CTC GAC GTT GTC ACT GAA     1074
Ala Thr Thr Gly Val Pro Cys Ala Ala Val Leu Asp Val Val Thr Glu
                 75                  80                  85
GCG GGA AGG GAC TGG CTG CTA TTG GGC GAA GTG CCG GGG CAG GAT CTC     1122
Ala Gly Arg Asp Trp Leu Leu Leu Gly Glu Val Pro Gly Gln Asp Leu
             90                  95                 100
CTG TCA TCT CAC CTT GCT CCT GCC GAG AAA GTA TCC ATC ATG GCT GAT     1170
Leu Ser Ser His Leu Ala Pro Ala Glu Lys Val Ser Ile Met Ala Asp
        105                 110                 115
GCA ATG CGG CGG CTG CAT ACG CTT GAT CCG GCT ACC TGC CCA TTC GAC     1218
Ala Met Arg Arg Leu His Thr Leu Asp Pro Ala Thr Cys Pro Phe Asp
    120                 125                 130
```

| | | | | | | | | | | | | | | | | |
|---|---|---|---|---|---|---|---|---|---|---|---|---|---|---|---|---|
| CAC | CAA | GCG | AAA | CAT | CGC | ATC | GAG | CGA | GCA | CGT | ACT | CGG | ATG | GAA | GCC | 1266 |
| His | Gln | Ala | Lys | His | Arg | Ile | Glu | Arg | Ala | Arg | Thr | Arg | Met | Glu | Ala | |
| 135 | | | | 140 | | | | 145 | | | | | | 150 | | |
| GGT | CTT | GTC | GAT | CAG | GAT | GAT | CTG | GAC | GAA | GAG | CAT | CAG | GGG | CTC | GCG | 1314 |
| Gly | Leu | Val | Asp | Gln | Asp | Asp | Leu | Asp | Glu | Glu | His | Gln | Gly | Leu | Ala | |
| | | | | 155 | | | | 160 | | | | | 165 | | | |
| CCA | GCC | GAA | CTG | TTC | GCC | AGG | CTC | AAG | GCG | CGC | ATG | CCC | GAC | GGC | GAG | 1362 |
| Pro | Ala | Glu | Leu | Phe | Ala | Arg | Leu | Lys | Ala | Arg | Met | Pro | Asp | Gly | Glu | |
| | | | 170 | | | | 175 | | | | | 180 | | | | |
| GAT | CTC | GTC | GTG | ACC | CAT | GGC | GAT | GCC | TGC | TTG | CCG | AAT | ATC | ATG | GTG | 1410 |
| Asp | Leu | Val | Val | Thr | His | Gly | Asp | Ala | Cys | Leu | Pro | Asn | Ile | Met | Val | |
| | | 185 | | | | 190 | | | | | 195 | | | | | |
| GAA | AAT | GGC | CGC | TTT | TCT | GGA | TTC | ATC | GAC | TGT | GGC | CGG | CTG | GGT | GTG | 1458 |
| Glu | Asn | Gly | Arg | Phe | Ser | Gly | Phe | Ile | Asp | Cys | Gly | Arg | Leu | Gly | Val | |
| | 200 | | | | 205 | | | | | 210 | | | | | | |
| GCG | GAC | CGC | TAT | CAG | GAC | ATA | GCG | TTG | GCT | ACC | CGT | GAT | ATT | GCT | GAA | 1506 |
| Ala | Asp | Arg | Tyr | Gln | Asp | Ile | Ala | Leu | Ala | Thr | Arg | Asp | Ile | Ala | Glu | |
| 215 | | | | 220 | | | | 225 | | | | | | 230 | | |
| GAG | CTT | GGC | GGC | GAA | TGG | GCT | GAC | CGC | TTC | CTC | GTG | CTT | TAC | GGT | ATC | 1554 |
| Glu | Leu | Gly | Gly | Glu | Trp | Ala | Asp | Arg | Phe | Leu | Val | Leu | Tyr | Gly | Ile | |
| | | | | 235 | | | | | 240 | | | | | 245 | | |
| GCC | GCT | CCC | GAT | TCG | CAG | CGC | ATC | GCC | TTC | TAT | CGC | CTT | CTT | GAC | GAG | 1602 |
| Ala | Ala | Pro | Asp | Ser | Gln | Arg | Ile | Ala | Phe | Tyr | Arg | Leu | Leu | Asp | Glu | |
| | | | 250 | | | | 255 | | | | | 260 | | | | |
| TTC | TTC | TGAGCAAGCT | | TTGGAGGGTT | | GATAAAAAAT | | AGGGGGAAAT | | AAACTGGTTT | | | | | | 1658 |
| Phe | Phe | | | | | | | | | | | | | | | |

```
GATTCCAGTT  TGAATTTATC  TATTTTTAGA  AATGTAGCTC  GGTAATTCTT  TACTTTTAGG     1718
ATTGCTTTTC  ATTAGTGAAA  TGTATTTGTT  AGGTCCAGGC  CTTACATCGT  ACTGTGAATA     1778
TTACAATTTT  TGACTTATTT  GTAGGAGGGG  AGAGAACACC  AAATATTGGT  GACAGAATGA     1838
GCCATTACAT  TACCACATCA  GATTATGGTA  GAGAGTTGAT  TGAATGTACT  CTCAAATATT     1898
TAACCCTCAA  ATATTGACTA  TATTAAGAGT  GCACTAACAG  ATGACCTATA  GACCCCAAAA     1958
ATTTCCTATC  TACCGTATAT  CTCTGAGCAT  AACCATTAAC  ACGATTTTGA  TATGTGGTGA     2018
GAACTTTTGA  TGGGACAAAT  TTTTGCCTAT  TGAGTGACAC  ACCAAAACCT  TCAGAAGAAG     2078
GTAAGCTTTT  TGAAGTATAT  TATCCGTTTA  GTCGAGAATC  GCTTAGTTTT  CAAAATATAC     2138
GCAGTTCAAA  AGTAGGGTGG  GTCTTATTAT  CCGTGGGGTC  TTATGCTCAG  AGATATACGG     2198
TATTATGTTT  TCATAGCTTC  ACTAGT                                             2224
```

( 2 ) INFORMATION FOR SEQ ID NO:9:

( i ) SEQUENCE CHARACTERISTICS:
        ( A ) LENGTH: 264 amino acids
        ( B ) TYPE: amino acid
        ( D ) TOPOLOGY: linear ( i i ) MOLECULE TYPE: protein ( x i ) SEQUENCE DESCRIPTION: SEQ ID NO:9:

| | | | | | | | | | | | | | | |
|---|---|---|---|---|---|---|---|---|---|---|---|---|---|---|
| Met | Ile | Glu | Gln | Asp | Gly | Leu | His | Ala | Gly | Ser | Pro | Ala | Ala | Trp | Val |
| 1 | | | | 5 | | | | 10 | | | | | 15 | | |
| Glu | Arg | Leu | Phe | Gly | Tyr | Asp | Trp | Ala | Gln | Gln | Thr | Ile | Gly | Cys | Ser |
| | | | 20 | | | | 25 | | | | | 30 | | | |
| Asp | Ala | Ala | Val | Phe | Arg | Leu | Ser | Ala | Gln | Gly | Arg | Pro | Val | Leu | Phe |
| | | | 35 | | | | 40 | | | | | 45 | | | |
| Val | Lys | Thr | Asp | Leu | Ser | Gly | Ala | Leu | Asn | Glu | Leu | Gln | Asp | Glu | Ala |
| | 50 | | | | | 55 | | | | | 60 | | | | |

| | | | | | | | | | | | | | | |
|---|---|---|---|---|---|---|---|---|---|---|---|---|---|---|
| Ala<br>65 | Arg | Leu | Ser | Trp<br>70 | Leu | Ala | Thr | Gly | Val<br>75 | Pro | Cys | Ala | Ala | Val<br>80 |
| Leu | Asp | Val | Val | Thr<br>85 | Glu | Ala | Gly | Arg | Asp<br>90 | Trp | Leu | Leu | Leu | Gly<br>95 | Glu |
| Val | Pro | Gly | Gln<br>100 | Asp | Leu | Leu | Ser | Ser<br>105 | His | Leu | Ala | Pro<br>110 | Ala | Glu | Lys |
| Val | Ser | Ile<br>115 | Met | Ala | Asp | Ala | Met<br>120 | Arg | Arg | Leu | His | Thr<br>125 | Leu | Asp | Pro |
| Ala | Thr | Cys<br>130 | Pro | Phe | Asp | His<br>135 | Gln | Ala | Lys | His | Arg<br>140 | Ile | Glu | Arg | Ala |
| Arg<br>145 | Thr | Arg | Met | Glu | Ala<br>150 | Gly | Leu | Val | Asp | Gln<br>155 | Asp | Asp | Leu | Asp | Glu<br>160 |
| Glu | His | Gln | Gly | Leu<br>165 | Ala | Pro | Ala | Glu | Leu<br>170 | Phe | Ala | Arg | Leu | Lys<br>175 | Ala |
| Arg | Met | Pro | Asp<br>180 | Gly | Glu | Asp | Leu | Val<br>185 | Val | Thr | His | Gly | Asp<br>190 | Ala | Cys |
| Leu | Pro | Asn<br>195 | Ile | Met | Val | Glu | Asn<br>200 | Gly | Arg | Phe | Ser | Gly<br>205 | Phe | Ile | Asp |
| Cys | Gly<br>210 | Arg | Leu | Gly | Val | Ala<br>215 | Asp | Arg | Tyr | Gln | Asp<br>220 | Ile | Ala | Leu | Ala |
| Thr<br>225 | Arg | Asp | Ile | Ala | Glu<br>230 | Glu | Leu | Gly | Gly | Glu<br>235 | Trp | Ala | Asp | Arg | Phe<br>240 |
| Leu | Val | Leu | Tyr | Gly<br>245 | Ile | Ala | Ala | Pro | Asp<br>250 | Ser | Gln | Arg | Ile | Ala<br>255 | Phe |
| Tyr | Arg | Leu | Leu | Asp<br>260 | Glu | Phe | Phe | | | | | | | | |

( 2 ) INFORMATION FOR SEQ ID NO:10:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: primer
        ( B ) LOCATION: 1..19

( x i ) SEQUENCE DESCRIPTION: SEQ ID NO:10:

TTTCTCATGA TTGAACAAG                            19

( 2 ) INFORMATION FOR SEQ ID NO:11:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: primer
        ( B ) LOCATION: 1..28

( x i ) SEQUENCE DESCRIPTION: SEQ ID NO:11:

ACTCATGAAG CTTGCTCAGA AGAACTCG                 28

While various embodiments of the present invention have been described in detail, modifications and adaptations of those embodiments will be apparent to those skilled in the art. It is to be expressly understood, however, that such

37 modifications and adaptations are within the scope of the present invention, as set forth in the following claims.

What is claimed is:

1. A method to transform a chlorophyll C-containing alga, comprising introducing a recombinant molecule comprising a nucleic acid molecule encoding a dominant selectable marker operatively linked to an algal regulatory control sequence into a chlorophyll C-containing alga such that said marker is produced by the transformed alga, wherein the regulatory control sequence is selected from the group consisting of a *Cyclotella cryptica* acetyl-CoA carboxylase 5' untranslated regulatory control sequence, a *Cyclotella cryptica* acetyl-CoA carboxylase 3'-untranslated regulatory control sequence, and combinations thereof.

2. A method as claimed in claim 1, wherein said chlorophyll C-containing alga is of a class selected from the group consisting of Bacillariophyceae, Chrysophyceae, Phaeophyceae, Xanthophyceae, Raphidophyceae, Prymnesiophyceae and Cryptophyceae.

3. A method as claimed in claim 1, wherein said chlorophyll C-containing alga is a diatom.

4. A method as claimed in claim 1, wherein said chlorophyll C-containing alga is of a genus selected from the group consisting of Cyclotella, Navicula, Cylindrotheca, Phaeodactylum, Amphora, Chaetoceros, Nitzschia and Thalassiosira.

5. A method as claimed in claim 1, wherein said chlorophyll C-containing alga is of a genus selected from the group consisting of Cyclotella and Navicula.

6. A method as claimed in claim 1, wherein said chlorophyll C-containing algae is of a species selected from the group consisting of *Cyclotella cryptica* and *Navicula saprophila*.

7. A method as claimed in claim 1, wherein said dominant selectable marker is selected from the group consisting of a heterologous marker capable of conferring resistance to a compound to which said alga otherwise exhibits sensitivity and a homologous marker, wherein said homologous marker is a homologous modified protein or nucleic acid, said homologous marker being capable of conferring resistance to a compound to which said alga otherwise exhibits sensitivity.

8. A method as claimed in claim 1, further comprising:
a) culturing said transformed alga in the presence of a compound to which algal cells exhibit sensitivity if not transformed by said recombinant molecule and to which said dominant selectable marker provides resistance; and
b) isolating from said culture a transformed alga that is capable of growing in the presence of said compound.

9. The method of claim 7, wherein said compound is selected from the group consisting of a compound that inhibits translation, a compound that inhibits transcription, a compound that inhibits enzyme function, a compound that inhibits cell growth, a compound that inhibits cell division, and a compound that inhibits microtubule formation.

10. A method as claimed in claim 7, wherein said dominant selectable marker is selected from the group consisting of neomycin phosphotransferase, aminoglycoside phosphotransferase, aminoglycoside acetyltransferase, chloramphenicol acetyl transferase, hygromycin B phosphotransferase, bleomycin binding protein, phosphinothricin acetyltransferase, bromoxynil nitrilase, glyphosate-resistant 5-enolpyruvylshikimate-3-phosphate synthase, cryptopleurine-resistant ribosomal protein S14, emetine-resistant ribosomal protein S14, sulfonylurea-resistant acetolactate synthase, imidazolinone-resistant acetolactate synthase, streptomycin-resistant 16S ribosomal RNA, spectinomycin-resistant 16S ribosomal RNA, erythromycin-resistant 23S ribosomal RNA, and methyl benzimidazole-resistant tubulin.

11. A method as claimed in claim 1, further comprising introducing a recombinant molecule comprising a nucleic acid molecule encoding a product operatively linked to an algal regulatory control sequence into said alga such that said product is produced by said alga.

12. A method as claimed in claim 11, wherein said recombinant molecule comprising a nucleic acid molecule encoding a product is different from said recombinant molecule encoding a dominant selectable marker.

13. A method of claim 11, wherein said alga is selected from the group consisting of *Cyclotella cryptica* and *Navicula sapropila*.

14. A method as claimed in claim 11, wherein one or both of said regulatory control sequences is selected from the group consisting of a *C. cryptica* acetyl-CoA carboxylase 5'-untranslated regulatory control sequence, a *C. cryptica* acetyl-CoA carboxylase 3'-untranslated regulatory control sequence, and combinations thereof.

15. A method as claimed in claim 11, wherein one or both of said regulatory control sequences is selected from the group consisting of a nucleic acid molecule comprising about 816 nucleotides immediately upstream from the translation initiation site of a *C. cryptica* acetyl-CoA carboxylase gene, a nucleic acid molecule comprising about 445 nucleotides immediately upstream from the translation initiation site of a *C. cryptica* acetyl-CoA carboxylase gene, a nucleic acid molecule comprising about 594 nucleotides immediately downstream from the translation termination site of a *C. cryptica* acetyl-CoA carboxylase gene, and combinations thereof.

16. A method as claimed in claim 1, wherein said regulatory control sequence is selected from the group consisting of a nucleic acid molecule comprising about 816 nucleotides immediately upstream from the translation initiation site of a *C. cryptica* acetyl-CoA carboxylase gene, a nucleic acid molecule comprising about 445 nucleotides immediately upstream from the translation initiation site of a *C. cryptica* acetyl-CoA carboxylase gene, a nucleic acid molecule comprising about 594 nucleotides immediately downstream from the translation termination site of a *C. cryptica* acetyl-CoA carboxylase gene, and combinations thereof.

17. The method of claim 11, wherein said product is selected from the group consisting of an RNA molecule and a protein.

18. A method as claimed in claim 11, wherein said product is acetyl-CoA carboxylase.

19. A method as claimed in claim 1, wherein said transformed alga is capable of maintaining said recombinant molecule for at least about eight months when cultured on a non-selective medium.

20. A method as claimed in claim 1, wherein said recombinant molecule comprises a molecule selected from the group consisting of pACCNPT10, pACCNPT5.1, and pACCNPT4.

21. A method as claimed in claim 1, wherein said recombinant molecule is integrated at a location selected from the group consisting of the nuclear genome of said alga, a chloroplast genome of said alga and a mitochondrial genome of said alga.

22. A chimetic molecule comprising one or more *C. cryptica* acetyl-CoA carboxylase regulatory control sequences operatively linked to a nucleic acid molecule encoding a compound selected from the group consisting of a selectable marker, an RNA molecule and a protein, wherein said nucleic acid molecule is not naturally associated with one or more of said regulatory control sequences, and wherein said regulatory control sequences are selected from the group consisting of 5'-untranslated regulatory control sequences, 3'-untranslated regulatory control sequences, and combinations thereof.

23. The chimeric molecule of claim 22, wherein said regulatory control sequences are selected from the group consisting of transcription control sequences, translation control sequences and combinations thereof.

24. The chimeric molecule of claim 22, wherein said molecule comprises a nucleic acid molecule operatively linked to a 5'-untranslated regulatory control sequence derived from a C. cryptica acetyl-CoA carboxylase gene and to a 3'-untranslated regulatory control sequence derived from a C. cryptica acetyl-CoA carboxylase gene.

25. The chimeric molecule of claim 22, wherein said selectable marker is neomycin phosphotransferase.

26. The chimeric molecule as claimed in claim 22, wherein said selectable marker is a dominant selectable marker operatively linked to said one or more regulatory control sequences and wherein said dominant selectable marker is selected from the group consisting of neomycin phosphotransferase, aminoglycoside phosphotransferase, aminoglycoside acetyltransferase, hygrormycin B phosphotransferase, bleomycin binding protein, phosphinothricin acetyltransferase, bromoxynil nitrilase, glyphosate-resistant 5-enolpyruvylshikimate-3-phosphate synthase, emetine-resistant ribosomal protein S14, cryptopleurine-resistant ribosomal protein S14, sulfonylurea-resistant acetolactate synthase, imidazolinone-resistant acetolactate synthase, streptomycin-resistant 16S ribosomal RNA, spectinomycin-resistant 16S ribosomal RNA, erythromycin-resistant 23S ribosomal RNA, and methyl benzimidazole-resistant tubulin.

27. The chimeric molecule as claimed in claim 22, wherein said protein is acetyl-CoA carboxylase.

28. The chimeric molecule as claimed in claim 22, wherein said regulatory control sequence is selected from the group consisting of a nucleic acid molecule comprising about 816 nucleotides immediately upstream from the translation initiation site of the C. cryptica acetyl-CoA carboxylase gene, a nucleic acid molecule comprising about 445 nucleotides immediately upstream from the translation initiation site of the C. cryptica acetyl-CoA carboxylase gene, a nucleic acid molecule comprising about 594 nucleotides immediately downstream from the translation termination site of the C. cryptica acetyl-CoA carboxylase gene, and combinations thereof.

29. A recombinant chlorophyll C-containing algal strain, wherein said strain is selected from the group consisting of:

(a) a chlorophyll C-containing algal strain transformed with a chimeric molecule comprising one or more C. cryptica acetyl-CoA carboxylase regulatory control sequences operatively linked to a nucleic acid molecule encoding a compound selected from the group consisting of a selectable marker, an RNA molecule and a protein, wherein said nucleic acid molecule is not naturally associated with one or more of said regulatory control sequences; and (b) chlorophyll C-containing algal strain transformed with at least one additional copy of a homologous nucleic acid molecule; wherein the regulatory control sequences are selected from the group consisting of a Cyclotella cryptica acetyl-CoA carboxylase 5'-untranslated regulatory control sequence, a Cyclotella cryptica acetyl-CoA carboxylase 3'-untranslated regulatory control sequence, and combinations thereof.

30. A strain as claimed in claim 29, wherein said strain is transformed with a DNA sequence encoding acetyl-CoC carboxylase.

31. An isolated nucleic acid molecule comprising a nucleic acid sequence selected from the group consisting of sequences identified as SEQ ID NO:1, SEQ ID NO:2, SEQ ID NO:3 and homologues thereof wherein the regulatory control sequences of said homologues are selected from the group consisting of a Cyclotella cryptica acetyl-CoA carboxylase 5'-untranslated regulatory control sequence, a Cyclotella cryptica acetyl-CoA carboxylase 3'-untranslated regulatory control sequence, and combinations thereof; said homologues having a regulatory function of the nucleic acid sequence SEQ ID NO:1, SEQ ID NO:2 or SEQ ID NO:3.

* * * * *